United States Patent
Wu et al.

(10) Patent No.: US 8,680,064 B2
(45) Date of Patent: *Mar. 25, 2014

(54) SHRNA GENE THERAPY FOR TREATMENT OF ISCHEMIC HEART DISEASE

(75) Inventors: Joseph C. Wu, Palo Alto, CA (US); Mei Huang, Union City, CA (US); Amato J. Giaccia, Palo Alto, CA (US); Denise Chan, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/998,075

(22) PCT Filed: Sep. 15, 2009

(86) PCT No.: PCT/US2009/005147
§ 371 (c)(1),
(2), (4) Date: Sep. 14, 2011

(87) PCT Pub. No.: WO2010/030396
PCT Pub. Date: Mar. 18, 2010

(65) Prior Publication Data
US 2012/0004283 A1    Jan. 5, 2012

Related U.S. Application Data

(60) Provisional application No. 61/136,555, filed on Sep. 15, 2008.

(51) Int. Cl.
*A61K 48/00*    (2006.01)
*C12N 15/00*    (2006.01)

(52) U.S. Cl.
USPC ..................... 514/44 R; 435/320.1

(58) Field of Classification Search
None
See application file for complete search history.

(56) References Cited

U.S. PATENT DOCUMENTS

| | | | |
|---|---|---|---|
| 2003/0203372 A1 | 10/2003 | Ward et al. | |
| 2006/0171924 A1* | 8/2006 | Luo et al. | 424/93.2 |
| 2007/0149470 A1* | 6/2007 | Kaspar et al. | 514/44 |
| 2007/0249550 A1 | 10/2007 | Sitkovsky et al. | |

FOREIGN PATENT DOCUMENTS

| | | |
|---|---|---|
| WO | WO 2007/076351 A2 | 7/2007 |
| WO | WO 2007076351 A2 * | 7/2007 |

OTHER PUBLICATIONS

Lee et al, The Biphasic Role of the Hypoxia-Inducible Factor Prolyl-4-Hydroxylase, PHD2, in Modulating Tumor-Forming Potential, May 2008, Mol Cancer Res, 6: 829-842.*
Natarajan et al, Activation of hypoxia-inducible factor-1 via prolyl-4 hydoxylase-2 gene silencing attenuates acute inflammatory responses in postischemic myocardium, Jun. 2007, Am J Physiol Heart Circ Physiol, 293: H1571-H1580.*
Ruan et al, A Hypoxia-Regulated Adeno-Associated Virus Vector for Cancer-Specific Gene Therapy, 2001, Neoplasia, vol. 3, 3: 255-263.*
Shamoto et al, WO 2005/116204, 2005 (only the first page of foreign document is included together with pp. 1, 142101-142103, 155639 of sequence listing, 6 pages total).*
Elbashir et al, Functional anatomy of siRNAs for mediating efficient RNAi in *Drosophila melanogaster* embryo lysate, 2001, the EMBO Journal, vol. 20, No. 23, pp. 6877-6888.*
Strausberg et al., '*Mus musculus* EGL nine homolog 1 (*C. elegans*), mRNA (cDNA clone Image: 30446815)' Genbank Accession No. BC083146, Oct. 20, 2004 [online] retrieved from the internet on [Feb. 10, 2010], retrieved from URL: ,http://www.ncbi.nlm.nih.gov/nuccore/53237088>, Sequence, nucleotides 434-452 and 564-582.
Dinchuk et al., '*Mus musculus* aspartyl beta-hydroxylase cardiac isoform 1 (Asph) mRNA, partial cds; alternatively spliced' Genbank Accession No. AF289491 [online] Dec. 18, 2000 retrieved on [Feb. 10, 2010], retrieved from the internet at URL: ,http://www.ncbi.nlm.nih.gov/nuccore/11878119., Sequence, nucleotides 174-192.
Lando et al., FIH-1 is an asparaginyl hydroxylase enzyme that regulates the transcriptional activity of hypoxia-inducible factor. gen. Dev. Jun. 15, 2002, vol. 16, No. 12, pp. 1466-1471; pp. 1466, col. 2, para 2.
Strausberg, et al., *Mus musculus* EGL nine homolog 1 (*C. elegans*), mRNA (cDNA done Image: 3046815) Genbank Accession No. BC083146, Oct. 20, 2004, retrieved from: URL: <http//www.ncbi.nlm.nih.gov/nucore/53237088>, Sequence nucleotides 434-452 and 564-582.
Dinchuk, et al. *Mus musculus* aspartyl beta-hydroxylase cardiac isoform 1 (Asph) mRNA, partial cds; alternatively spliced, Genbank Accession No. AF289491 [online], Dec. 18, 2000, retrieved from URL: <http://www.ncbi.nlm.nih.gov/nucore/11878119> Sequence, nucleotides 174-192.
Lando, et al., FIH-1 is an asparaginyl jydroxylase enzyme that regulates the traanscriptional activity of hypoxia-inducible factor., Gen. Dev. Jun. 15, 2002, vol. 16, No. 12, pp. 1466-1471; p. 1466, col. 2, para 2.

* cited by examiner

*Primary Examiner* — Tracy Vivlemore
*Assistant Examiner* — Kate Poliakova-Georgan
(74) *Attorney, Agent, or Firm* — William Beaumont, Juneau Partners

(57) ABSTRACT

Short hairpin RNA (shRNA) interference therapy targeting hypoxia inducible factor—lot (HIF-1 α) prolyl-4-hydroxylase protein (HIF-PHD2) is used for treatment of myocardial ischemia. This treatment can be followed noninvasively by molecular imaging. Provided are compositions comprising novel vectors encoding shRNA targeting the HIF-1α and asparaginyl hydroxylase genes. The vectors encoding shRNA are also useful for the treatment of cardiac diseases, peripheral vascular diseases and decubitis ulcers.

24 Claims, 12 Drawing Sheets

| | | |
|---|---|---|
| bFGF | Forward | 5'—CTTCAAGGACCCCAAGCGGGCTCTA—3' |
| | Reverse | 5'—CGAGTTTATACTGCCCAGTT—3' |
| Transferin | Forward | 5'—CTTCAAGGACCCCAAGCGGGCTCTAC—3' |
| | Reverse | 5'—GTTCGTTTCAGTGCCACATACCAAC—3' |
| FLT | Forward | 5'—TGAAGTCTGCTCGCTATTGGTA—3' |
| | Reverse | 5'—CTATGGTGCATGGTTCTGTTGTT—3' |
| KDR | Forward | 5'—GAAGCTACTGCCGTCCGATTGAG—3' |
| | Reverse | 5'—TGCTGGCTTTGGTGAGGTTTGAT—3' |
| TGF | Forward | 5'—AAATTCGACATGATCCAGGACT—3' |
| | Reverse | 5'—TGCACTTACACGACTTCACCACC—3' |
| PAI | Forward | 5'—ATGGCTCAGAGCAACAAGTTCAA—3' |
| | Reverse | 5'—GACAAAGGCTGTGGAGGAAGACG—3' |

Figure 9

SEQUENCE LISTING

```
<160> NUMBER OF SEQ ID NOS: 37

<210> SEQ ID NO 1
<211> LENGTH: 502
<212> TYPE: PRT
<213> ORGANISM: Homo sapiens

<400> SEQUENCE: 1

Met Ala Ala Ala Val Thr Gly Gln Arg Pro Glu Thr Ala Ala Ala
1               5                   10                  15

Glu Glu Ala Ser Arg Pro Gln Trp Ala Pro Asp His Cys Gln Ala
                20                  25                  30

Gln Ala Ala Ala Gly Leu Gly Asp Gly Glu Asp Ala Pro Val Arg Pro
            35                  40                  45

Leu Cys Lys Pro Arg Gly Ile Cys Ser Arg Ala Tyr Phe Leu Val Leu
    50                  55                  60

Met Val Phe Val His Leu Tyr Leu Gly Asn Val Leu Ala Leu Leu Leu
65                  70                  75                  80

Phe Val His Tyr Ser Asn Gly Asp Glu Ser Ser Asp Pro Gly Pro Gln
                85                  90                  95

His Arg Ala Gln Gly Pro Gly Pro Glu Pro Thr Leu Gly Pro Leu Thr
            100                 105                 110

Arg Leu Glu Gly Ile Lys Val Gly His Glu Arg Lys Val Gln Leu Val
        115                 120                 125

Thr Asp Arg Asp His Phe Ile Arg Thr Leu Ser Leu Lys Pro Leu Leu
    130                 135                 140

Phe Glu Ile Pro Gly Phe Leu Thr Asp Glu Glu Cys Arg Leu Ile Ile
145                 150                 155                 160

His Leu Ala Gln Met Lys Gly Leu Gln Arg Ser Gln Ile Leu Pro Thr
                165                 170                 175

Glu Glu Tyr Glu Glu Ala Met Ser Thr Met Gln Val Ser Gln Leu Asp
            180                 185                 190
```

```
Leu Phe Arg Leu Leu Asp Gln Asn Arg Asp Gly His Leu Gln Leu Arg
        195                 200                 205

Glu Val Leu Ala Gln Thr Arg Leu Gly Asn Gly Trp Trp Met Thr Pro
    210                 215                 220

Glu Ser Ile Gln Glu Met Tyr Ala Ala Ile Lys Ala Asp Pro Asp Gly
225                 230                 235                 240

Asp Gly Val Leu Ser Leu Gln Glu Phe Ser Asn Met Asp Leu Arg Asp
                245                 250                 255

Phe His Lys Tyr Met Arg Ser His Lys Ala Glu Ser Ser Glu Leu Val
            260                 265                 270

Arg Asn Ser His His Thr Trp Leu Tyr Gln Gly Glu Gly Ala His His
        275                 280                 285

Ile Met Arg Ala Ile Arg Gln Arg Val Leu Arg Leu Thr Arg Leu Ser
    290                 295                 300

Pro Glu Ile Val Glu Leu Ser Glu Pro Leu Gln Val Val Arg Tyr Gly
305                 310                 315                 320

Glu Gly Gly His Tyr His Ala His Val Asp Ser Gly Pro Val Tyr Pro
                325                 330                 335

Glu Thr Ile Cys Ser His Thr Lys Leu Val Ala Asn Glu Ser Val Pro
            340                 345                 350

Phe Glu Thr Ser Cys Arg Tyr Met Thr Val Leu Phe Tyr Leu Asn Asn
        355                 360                 365

Val Thr Gly Gly Gly Glu Thr Val Phe Pro Val Ala Asp Asn Arg Thr
    370                 375                 380

Tyr Asp Glu Met Ser Leu Ile Gln Asp Val Asp Leu Arg Asp Arg Thr
385                 390                 395                 400

Arg Arg His Cys Asp Lys Gly Asn Leu Arg Val Lys Pro Gln Gln Gly
                405                 410                 415

Thr Ala Val Phe Trp Tyr Asn Tyr Leu Pro Asp Gly Gln Gly Trp Val
            420                 425                 430

Gly Asp Val Asp Asp Tyr Ser Leu His Gly Gly Cys Leu Val Thr Arg
        435                 440                 445

Gly Thr Lys Trp Ile Ala Asn Asn Trp Ile Asn Val Asp Pro Ser Arg
    450                 455                 460

Ala Arg Gln Ala Leu Phe Gln Gln Glu Met Ala Arg Leu Ala Arg Glu
465                 470                 475                 480

Gly Gly Thr Asp Ser Gln Pro Glu Trp Ala Leu Asp Arg Ala Tyr Arg
                485                 490                 495

Asp Ala Arg Val Glu Leu
            500

<210> SEQ ID NO 2
<211> LENGTH: 2111
<212> TYPE: DNA
<213> ORGANISM: Homo sapiens

<400> SEQUENCE: 2
agagggcgtc ttcacgcagg caccgagaag ctcccactag tgtatgcctt aatggtgccg    60
ctcttgtccg cgtctacgct tgggaccttg gcttctgact tggagagtgt acagctctgc   120
ccgacggcaa cccagcttgg gaagagaagc cccagcgtgg gctggggctc aaggcgcagg   180
aaggccgagc ccggcgcgga cgcaggcggc tccggcggg ctcagcaccc ccaggcaccg   240
tctcctagtg accgcggcgc tcgcgggcct ggcggccgtt gtccgggcga ctgcgcagcg   300
cgggcacccc cgcggcccct ccctgggcg cgcgcgcgac ctgggtgcca tggcggcagc   360
```

```
ggcggtgaca ggccagcggc ctgagaccgc ggcggccgag gaggcctcga ggccgcagtg      420
ggcgccgcca gaccactgcc aggctcaggc ggcggccggg ctgggcgacg gcgaggacgc      480
accggtgcgt ccgctgtgca agccccgcgg catctgctcg cgcgcctact tcctggtgct      540
gatggtgttc gtgcacctgt acctgggtaa cgtgctggcg ctgctgctct tcgtgcacta      600
cagcaacggc gacgaaagca gcgatcccgg gccccaacac cgtgcccagg gccccgggcc      660
cgagcccacc ttaggtcccc tcacccggct ggagggcatc aaggtggggc acgagcgtaa      720
ggtccagctg gtcaccgaca gggatcactt catccgaacc ctcagcctca gccgctgct       780 cttcgaaatc cccggcttcc tgactgatga agagtgtcgg ctcatcatcc atctggcgca      840
gatgaagggg ttacagcgca gccagatcct gcctactgaa gagtatgaag aggcaatgag      900
cactatgcag gtcagccagc tggacctctt ccggctgctg gaccagaacc gtgatgggca      960
ccttcagctc cgtgaggttc tggcccagac tcgcctggga aatggatggt ggatgactcc     1020
agagagcatt caggagatgt acgccgcgat caaggctgac cctgatggtg acggagtgct     1080
gagtctgcag gagttctcca acatggacct tcgggacttc cacaagtaca tgaggagcca     1140
caaggcagag tccagtgagc tggtgcggaa cagccaccat acctggctct accagggtga     1200
gggtgcccac cacatcatgc gtgccatccg ccagagggtg ctgcgcctca ctcgcctgtc     1260
gcctgagatc gtggagctca gcgagccgct gcaggttgtt cgatatggtg agggggggcca    1320 ctaccatgcc cacgtggaca gtgggcctgt gtacccagag accatctgct cccataccaa     1380
gctggtagcc aacgagtctg taccttcga gacctcctgc cgctacatga cagtgctgtt      1440
ttatttgaac aacgtcactg gtgggggcga gactgttttc cctgtagcag ataacagaac     1500
ctacgatgaa atgagtctga ttcaggatga cgtggacctc cgtgacacac ggaggcactg     1560
tgacaaggga aacctgcgtg tcaagccccca acagggcaca gcagtcttct ggtacaacta    1620
cctgcctgat gggcaaggtt gggtgggtga cgtagacgac tactcgctgc acggggctg      1680 cctggtcacg cgcggcacca gtggattgc caacaactgg attaatgtgg accccagccg      1740
agcgcggcaa cgctgttcc aacaggagat ggccccgcctt gcccgagaag ggggcaccga    1800
ctcacagccc gagtgggctc tggaccgggc ctaccgcgat gcgcgcgtgg aactctgagg     1860
gaagagttag ccccggttcc cagccgcggg tcgccagttg cccaagatca ggggtccggc     1920
tgtccttctg tcctgctgca gactaaaggt ctggccaatg tcttgccccca ccccgccagc    1980 cgcgatacgg cgcagttcct atattcatgt tatttattgt gtactgactc catctgcccc     2040
gtcaaataaa aaaccacaag gttcgagccg ccgggcccga caaactccgg gtcggcgaaa     2100
aaaaaaaaaa a                                                          2111
```

```
<210> SEQ ID NO 3
<211> LENGTH: 534
<212> TYPE: PRT
<213> ORGANISM: Homo sapiens

<400> SEQUENCE: 3

Met Ile Trp Tyr Ile Leu Ile Gly Ile Leu Leu Pro Gln Ser Leu
1               5                   10                  15

Ala His Pro Gly Phe Phe Thr Ser Ile Gly Gln Met Thr Asp Leu Ile
                20                  25                  30

His Thr Glu Lys Asp Leu Val Thr Ser Leu Lys Asp Tyr Ile Lys Ala
            35                  40                  45

Glu Glu Asp Lys Leu Glu Gln Ile Lys Lys Trp Ala Glu Lys Leu Asp
        50                  55                  60
```

-continued

```
Arg Leu Thr Ser Thr Ala Thr Lys Asp Pro Glu Gly Phe Val Gly His
 65                  70                  75                  80

Pro Val Asn Ala Phe Lys Leu Met Lys Arg Leu Asn Thr Glu Trp Ser
                 85                  90                  95

Glu Leu Glu Asn Leu Val Leu Lys Asp Met Ser Asp Gly Phe Ile Ser
            100                 105                 110

Asn Leu Thr Ile Gln Arg Gln Tyr Phe Pro Asn Asp Glu Asp Gln Val
        115                 120                 125

Gly Ala Ala Lys Ala Leu Leu Arg Leu Gln Asp Thr Tyr Asn Leu Asp
    130                 135                 140

Thr Asp Thr Ile Ser Lys Gly Asn Leu Pro Gly Val Lys His Lys Ser
145                 150                 155                 160

Phe Leu Thr Ala Glu Asp Cys Phe Glu Leu Gly Lys Val Ala Tyr Thr
                165                 170                 175

Glu Ala Asp Tyr Tyr His Thr Glu Leu Trp Met Glu Gln Ala Leu Arg
            180                 185                 190

Gln Leu Asp Glu Gly Glu Ile Ser Thr Ile Asp Lys Val Ser Val Leu
        195                 200                 205

Asp Tyr Leu Ser Tyr Ala Val Tyr Gln Gln Gly Asp Leu Asp Lys Ala
    210                 215                 220

Leu Leu Leu Thr Lys Lys Leu Glu Leu Asp Pro Glu His Gln Arg
225                 230                 235                 240

Ala Asn Gly Asn Leu Lys Tyr Phe Glu Tyr Ile Met Ala Lys Glu Lys
                245                 250                 255

Asp Val Asn Lys Ser Ala Ser Asp Gln Ser Asp Gln Lys Thr Thr
            260                 265                 270

Pro Lys Lys Lys Gly Val Ala Val Asp Tyr Leu Pro Glu Arg Gln Lys
        275                 280                 285

Tyr Glu Met Leu Cys Arg Gly Glu Gly Ile Lys Met Thr Pro Arg Arg
    290                 295                 300

Gln Lys Lys Leu Phe Cys Arg Tyr His Asp Gly Asn Arg Asn Pro Lys
305                 310                 315                 320

Phe Ile Leu Ala Pro Ala Lys Gln Glu Asp Glu Trp Asp Lys Pro Arg
                325                 330                 335

Ile Ile Arg Phe His Asp Ile Ile Ser Asp Ala Glu Ile Glu Ile Val
            340                 345                 350

Lys Asp Leu Ala Lys Pro Arg Leu Arg Arg Ala Thr Ile Ser Asn Pro
        355                 360                 365

Ile Thr Gly Asp Leu Glu Thr Val His Tyr Arg Ile Ser Lys Ser Ala
    370                 375                 380

Trp Leu Ser Gly Tyr Glu Asn Pro Val Val Ser Arg Ile Asn Met Arg
385                 390                 395                 400

Ile Gln Asp Leu Thr Gly Leu Asp Val Ser Thr Ala Glu Glu Leu Gln
                405                 410                 415

Val Ala Asn Tyr Gly Val Gly Gly Gln Tyr Glu Pro His Phe Asp Phe
            420                 425                 430

Ala Arg Lys Asp Glu Pro Asp Ala Phe Lys Glu Leu Gly Thr Gly Asn
        435                 440                 445

Arg Ile Ala Thr Trp Leu Phe Tyr Met Ser Asp Val Ser Ala Gly Gly
    450                 455                 460

Ala Thr Val Phe Pro Glu Val Gly Ala Ser Val Trp Pro Lys Lys Gly
465                 470                 475                 480

Thr Ala Val Phe Trp Tyr Asn Leu Phe Ala Ser Gly Glu Gly Asp Tyr
                485                 490                 495
```

```
Ser Thr Arg His Ala Ala Cys Pro Val Leu Val Gly Asn Lys Trp Val
            500                 505                 510

Ser Asn Lys Trp Leu His Glu Arg Gly Gln Glu Phe Arg Arg Pro Cys
            515                 520                 525

Thr Leu Ser Glu Leu Glu
        530

<210> SEQ ID NO 4
<211> LENGTH: 2752
<212> TYPE: DNA
<213> ORGANISM: Homo sapiens

<400> SEQUENCE: 4
gcccagtcgc gccgccagcg ggctgagggt aggaagtagc cgctccgagt ggaggcgact      60
gggggctgaa gagcgcgccg ccctctcgtc ccactttcca ggtgtgtgat cctgtaaaat     120
taaatcttcc aagatgatct ggtatatatt aattatagga attctgcttc cccagtcttt     180
ggctcatcca ggctttttta cttcaattgg tcagatgact gatttgatcc atactgagaa     240
agatctggtg acttctctga aagattatat taaggcagaa gaggacaagt tagaacaaat     300
aaaaaaatgg gcagagaagt tagatcggct aactagtaca gcgacaaaag atccagaagg     360
atttgttggg catccagtaa atgcattcaa attaatgaaa cgtctgaata ctgagtggag     420
tgagttggag aatctggtcc ttaaggatat gtcagatggc tttatctcta acctaaccat     480
tcagagacag tactttccta atgatgaaga tcaggttggg gcagccaaag ctctgttacg     540
tctccaggat acctacaatt tggatacaga taccatctca aagggtaatc ttccaggagt     600
gaaacacaaa tcttttctaa cggctgagga ctgctttgag ttgggcaaag tggcctatac     660
agaagcagat tattaccata cggaactgtg gatggaacaa gccctaaggc aactggatga     720
aggcgagatt tctaccatag ataaagtctc tgttctagat tatttgagct atgcggtata     780
tcagcaggga gacctggata aggcactttt gctcacaaag aagcttcttg aactagatcc     840
tgaacatcag agagctaatg gtaacttaaa atattttgag tatataatgg ctaaagaaaa     900
agatgtcaat aagtctgctt cagatgacca atctgatcag aaaactacac aaagaaaaa      960 aggggttgct gtggattacc tgccagagag acagaagtac gaaatgctgt gccgtgggga    1020
gggtatcaaa atgaccccctc ggagacagaa aaaactcttt tgccgctacc atgatggaaa    1080
ccgtaatcct aaatttattc tggctccagc taaacaggag gatgaatggg acaagcctcg    1140
tattattcgc ttccatgata ttatttctga tgcagaaatt gaaatcgtca agacctagc     1200 aaaaccaagg ctgaggcgag ccaccatttc aaacccaata acaggagact ggagacggt    1260 acattacaga attagcaaaa gtgcctggct ctctggctat gaaaatcctg tggtgtctcg    1320
aattaatatg agaatacaag atctaacagg actagatgtt ccacagcag aggaattaca    1380 ggtagcaaat tatggagttg aggacagta tgaaccccat tttgactttg cacgaaaga    1440 tgagccagat gctttcaaag agctggggac aggaaataga attgctacat ggctgtttta    1500
tatgagtgat gtgtctgcag gaggagccac tgttttttcct gaagttggag ctagtgtttg    1560
gcccaaaaaa ggaactgctg tttttctggta taatctgttt gccagtggag aaggagatta    1620
tagtacacgg catgcagcct gtccagtgct agttggcaac aaatgggtat ccaataaatg    1680
gctccatgaa cgtggacaag aatttcgaag accttgtacg ttgtcagaat ggaatgaca    1740 aacaggcttc cctttttctc ctattgttgt actcttatgt gtctgatata cacatttcct    1800
agtcttaact ttcaggagtt tacaattgac taacactcca tgattgattc agtcatgaac    1860
```

-continued

```
ctcatcccat gtttcatctg tggacaattg cttactttgt gggttctttt aaaagtaaca    1920
cgaaatcatc atattgcata aaaccttaaa gttctgttgg tatcacagaa gacaaggcag    1980
agtttaaagt gaggaatttt atatttaaag aacttttggg ttggataaaa acataatttg    2040
agcatccagt tttagtattt cactacatct cagttggtgg gtgttaagct agaatgggct    2100
gtgtgatagg aaacaaatgc cttacagatg tgcctaggtg ttctgtttac ctagtgtctt    2160
actctgtttt ctggatctga agactagtaa taaactagga cactaactgg gttccatgtg    2220
attgcccttt catatgatct tctaagttga ttttttttcct cccaagtctt ttttaaagaa    2280
agtatactgt attttaccaa ccccctctct tttcttttag ctcctctgtg gtgaattaaa    2340
cgtacttgag ttaaaatatt tcgattttt tttttttttt aatggaaagt cctgcataac     2400
aacactgggc cttcttaact aaaatgctca ccacttagcc tgtttttta tcccttttt      2460 aaaatgacag atgattttgt tcaggaattt tgctgttttt cttagtgcta ataccttgcc    2520
tcttattcct gctacagcag ggtggtaata ttggcattct gattaaatac tgtgccttag    2580
gagactggaa gtttaaaaat gtacaagtcc tttcagtgat gagggaattg atttttttta    2640
aaagtctttt tcttagaaag ccaaaatgtt tgttttttta agattctgaa atgtgttgtg    2700
acaacaatga cctatttatg atcttaaatc ttttttaaaa aaaaaaaaa aa             2752
```

<210> SEQ ID NO 5
<211> LENGTH: 535
<212> TYPE: PRT
<213> ORGANISM: Homo sapiens

<400> SEQUENCE: 5

```
Met Lys Leu Trp Val Ser Ala Leu Leu Met Ala Trp Phe Gly Val Leu
1               5                   10                  15

Ser Cys Val Gln Ala Glu Phe Phe Thr Ser Ile Gly His Met Thr Asp
            20                  25                  30

Leu Ile Tyr Ala Glu Lys Glu Leu Val Gln Ser Leu Lys Glu Tyr Ile
        35                  40                  45

Leu Val Glu Glu Ala Lys Leu Ser Lys Ile Lys Ser Trp Ala Asn Lys
    50                  55                  60

Met Glu Ala Leu Thr Ser Lys Ser Ala Ala Asp Ala Glu Gly Tyr Leu
65                  70                  75                  80

Ala His Pro Val Asn Ala Tyr Lys Leu Val Lys Arg Leu Asn Thr Asp
                85                  90                  95

Trp Pro Ala Leu Glu Asp Leu Val Leu Gln Asp Ser Ala Ala Gly Phe
            100                 105                 110

Ile Ala Asn Leu Ser Val Gln Arg Gln Phe Phe Pro Thr Asp Glu Asp
        115                 120                 125

Glu Ile Gly Ala Ala Lys Ala Leu Met Arg Leu Gln Asp Thr Tyr Arg
    130                 135                 140

Leu Asp Pro Gly Thr Ile Ser Arg Gly Glu Leu Pro Gly Thr Lys Tyr
145                 150                 155                 160

Gln Ala Met Leu Ser Val Asp Asp Cys Phe Gly Met Gly Arg Ser Ala
                165                 170                 175

Tyr Asn Glu Gly Asp Tyr Tyr His Thr Val Leu Trp Met Glu Gln Val
            180                 185                 190

Leu Lys Gln Leu Asp Ala Gly Glu Glu Ala Thr Thr Thr Lys Ser Gln
        195                 200                 205

Val Leu Asp Tyr Leu Ser Tyr Ala Val Phe Gln Leu Gly Asp Leu His
    210                 215                 220
```

```
Arg Ala Leu Glu Leu Thr Arg Arg Leu Leu Ser Leu Asp Pro Ser His
225                 230                 235                 240

Glu Arg Ala Gly Gly Asn Leu Arg Tyr Phe Glu Gln Leu Leu Glu Glu
            245                 250                 255

Glu Arg Glu Lys Thr Leu Thr Asn Gln Thr Glu Ala Glu Leu Ala Thr
        260                 265                 270

Pro Glu Gly Ile Tyr Glu Arg Pro Val Asp Tyr Leu Pro Glu Arg Asp
    275                 280                 285

Val Tyr Glu Ser Leu Cys Arg Gly Glu Gly Val Lys Leu Thr Pro Arg
290                 295                 300

Arg Gln Lys Arg Leu Phe Cys Arg Tyr His His Gly Asn Arg Ala Pro
305                 310                 315                 320

Gln Leu Leu Ile Ala Pro Phe Lys Glu Glu Asp Glu Trp Asp Ser Pro
            325                 330                 335

His Ile Val Arg Tyr Tyr Asp Val Met Ser Asp Glu Ile Glu Arg
        340                 345                 350

Ile Lys Glu Ile Ala Lys Pro Lys Leu Ala Arg Ala Thr Val Arg Asp
    355                 360                 365

Pro Lys Thr Gly Val Leu Thr Val Ala Ser Tyr Arg Val Ser Lys Ser
370                 375                 380

Ser Trp Leu Glu Glu Asp Asp Asp Pro Val Val Ala Arg Val Asn Arg
385                 390                 395                 400

Arg Met Gln His Ile Thr Gly Leu Thr Val Lys Thr Ala Glu Leu Leu
            405                 410                 415

Gln Val Ala Asn Tyr Gly Val Gly Gly Gln Tyr Glu Pro His Phe Asp
        420                 425                 430

Phe Ser Arg Asn Asp Glu Arg Asp Thr Phe Lys His Leu Gly Thr Gly
    435                 440                 445

Asn Arg Val Ala Thr Phe Leu Asn Tyr Met Ser Asp Val Glu Ala Gly
450                 455                 460

Gly Ala Thr Val Phe Pro Asp Leu Gly Ala Ala Ile Trp Pro Lys Lys
465                 470                 475                 480

Gly Thr Ala Val Phe Trp Tyr Asn Leu Leu Arg Ser Gly Glu Gly Asp
            485                 490                 495

Tyr Arg Thr Arg His Ala Ala Cys Pro Val Leu Val Gly Cys Lys Trp
        500                 505                 510

Val Ser Asn Lys Trp Phe His Glu Arg Gly Gln Glu Phe Leu Arg Pro
    515                 520                 525

Cys Gly Ser Thr Glu Val Asp
530                 535

<210> SEQ ID NO 6
<211> LENGTH: 2588
<212> TYPE: DNA
<213> ORGANISM: Homo sapiens

<400> SEQUENCE: 6
agcgttgttt tccttggca gctgcggaga cccgtgataa ttcgttaact aattcaacaa    60
acgggaccct tctgtgtgcc agaaaccgca agcagttgct aacccagtgg gacaggcgga   120
ttggaagagc gggaaggtcc tggcccagag cagtgtggtg agcgctgtgc tggaagggaa   180
tgcgggcagt gggtacttgg tagagcactg actgcctccg gccagaggac ttcccggagg   240
aggtgaccca tgagctggag tggtcagagg aaggctggca aagggcatc gtggacagag   300 gaacagccta tgtgagtggg agcagagacc ttggccaatg ccattcctta tggccttgta   360
```

| | |
|---|---|
| gtggaagcaa ggtgatgggg aaggaacact gtaggggata gctgtccacg gacgctgtct | 420 |
| acaagaccct ggagtgagat aacgtgcctg gtactgtgcc ctgcatgtgt aagatgccca | 480 |
| gttgaccttc gcagcaggag cctggatcag ggcacttcct gcctcaggta ttgctggaca | 540 |
| gcccagacac ttccctctgt gaccatgaaa ctctgggtgt ctgcattgct gatggcctgg | 600 |
| tttggtgtcc tgagctgtgt gcaggccgaa ttcttcacct ctattgggca catgactgac | 660 |
| ctgatttatg cagagaaaga gctggtgcag tctctgaaag agtacatcct tgtggaggaa | 720 |
| gccaagcttt ccaagattaa gagctgggcc aacaaaatgg aagccttgac tagcaagtca | 780 |
| gctgctgatg ctgagggcta cctggctcac cctgtgaatg cctacaaact ggtgaagcgg | 840 |
| ctaaacacag actggcctgc gctggaggac cttgtcctgc aggactcagc tgcaggtttt | 900 |
| atcgccaacc tctctgtgca gcggcagttc ttccccactg atgaggacga ataggagct | 960 |
| gccaaagccc tgatgagact tcaggacaca tacaggctgg acccaggcac aatttccaga | 1020 |
| ggggaacttc caggaaccaa gtaccaggca atgctgagtg tggatgactg ctttgggatg | 1080 |
| ggccgctcgg cctacaatga aggggactat tatcatacgg tgttgtggat ggagcaggtg | 1140 |
| ctaaagcagc ttgatgccgg ggaggaggcc accacaacca agtcacaggt gctggactac | 1200 |
| ctcagctatg ctgtcttcca gttgggtgat ctgcaccgtg ccctggagct cacccgccgc | 1260 |
| ctgctctccc ttgacccaag ccacgaacga gctggaggga atctgcggta ctttgagcag | 1320 |
| ttattggagg aagagagaga aaaaacgtta acaaatcaga cagaagctga gctagcaacc | 1380 |
| ccagaaggca tctatgagag gcctgtggac tacctgcctg agggatgt ttacgagagc | 1440 |
| ctctgtcgtg gggagggtgt caaactgaca ccccgtagac agaagaggct tttctgtagg | 1500 |
| taccaccatg gcaacagggc cccacagctg ctcattgccc ccttcaaaga ggaggacgag | 1560 |
| tgggacagcc cgcacatcgt caggtactac gatgtcatgt ctgatgagga aatcgagagg | 1620 |
| atcaaggaga tcgcaaaacc taaacttgca cgagccaccg ttcgtgatcc caagacagga | 1680 |
| gtcctcactg tcgccagcta ccgggtttcc aaaagctcct ggctagagga agatgatgac | 1740 |
| cctgttgtgg cccgagtaaa tcgtcggatg cagcatatca cagggttaac agtaaagact | 1800 |
| gcagaattgt tacaggttgc aaattatgga gtgggaggac agtatgaacc gcacttcgac | 1860 |
| ttctctagga atgatgagcg agatactttc aagcatttag ggacggggaa tcgtgtggct | 1920 |
| actttcttaa actacatgag tgatgtagaa gctggtggtg ccaccgtctt ccctgatctg | 1980 |
| ggggctgcaa tttggcctaa gaagggtaca gctgtgttct ggtacaacct cttgcggagc | 2040 |
| ggggaaggtg actaccgaac aagacatgct gcctgccctg tgcttgtggg ctgcaagtgg | 2100 |
| gtctccaata gtggttccat gaacgagga caggagttct tgagaccttg tggatcaaca | 2160 |
| gaagttgact gacatccttt tctgtccttc cccttcctgg tccttcagcc catgtcaacg | 2220 |
| tgacagacac ctttgtatgt tcctttgtat gttcctatca ggctgatttt tggagaaatg | 2280 |
| aatgtttgtc tggagcagag ggagaccata ctagggcgac tcctgtgtga ctgaagtccc | 2340 |
| agcccttcca ttcagcctgt gccatccctg gccccaaggc taggatcaaa gtggctgcag | 2400 |
| cagagttagc tgtctagcgc ctagcaaggt gcctttgtac ctcaggtgtt ttaggtgtga | 2460 |
| gatgtttcag tgaaccaaag ttctgatacc ttgtttacat gtttgttttt atggcatttc | 2520 |
| tatctattgt ggctttacca aaaataaaa tgtccctacc agaagcctta aaaaaaaaa | 2580 |
| aaaaaaaa | 2588 |

<210> SEQ ID NO 7
<211> LENGTH: 535
<212> TYPE: PRT

<213> ORGANISM: Rattus norvegicus

<400> SEQUENCE: 7

```
Met Lys Leu Gln Val Leu Val Leu Leu Met Ser Trp Phe Gly Val Leu
 1               5                  10                  15

Ser Trp Val Gln Ala Glu Phe Phe Thr Ser Ile Gly His Met Thr Asp
            20                  25                  30

Leu Ile Tyr Ala Glu Lys Asp Leu Val Gln Ser Leu Lys Glu Tyr Ile
        35                  40                  45

Leu Ala Glu Ala Lys Leu Ser Lys Ile Lys Ser Trp Ala Ser Lys
    50                  55                  60

Met Glu Ala Leu Thr Ser Lys Ser Ala Ala Asp Pro Glu Gly Tyr Leu
65                  70                  75                  80

Ala His Pro Val Asn Ala Tyr Lys Leu Val Lys Arg Leu Asn Thr Asp
                85                  90                  95

Trp Pro Ala Leu Gly Asp Leu Val Leu Gln Asp Ala Ala Gly Phe
            100                 105                 110

Val Ala Asn Leu Ser Val Gln Arg Gln Phe Phe Pro Thr Asp Glu Asp
            115                 120                 125

Glu Ser Gly Ala Ala Arg Ala Leu Met Arg Leu Gln Asp Thr Tyr Lys
        130                 135                 140

Leu Asp Pro Asp Met Ile Ser Arg Gly Glu Leu Pro Gly Thr Lys Tyr
145                 150                 155                 160

Gln Ala Met Leu Ser Val Asp Asp Cys Phe Gly Met Gly Arg Ser Ala
                165                 170                 175

Tyr Asn Glu Gly Asp Tyr Tyr His Thr Val Leu Trp Met Glu Gln Val
            180                 185                 190

Leu Lys Gln Leu Asp Ala Gly Glu Glu Ala Thr Val Thr Lys Ser Leu
        195                 200                 205

Val Leu Asp Tyr Leu Ser Tyr Ala Val Phe Gln Leu Gly Asp Leu His
    210                 215                 220

Arg Ala Val Glu Leu Thr Arg Arg Leu Leu Ser Leu Asp Pro Ser His
225                 230                 235                 240

Glu Arg Ala Gly Gly Asn Leu Arg Tyr Phe Glu Arg Leu Leu Glu Glu
                245                 250                 255

Glu Arg Gly Lys Ser Leu Ser Asn Gln Thr Asp Ala Gly Leu Ala Ser
            260                 265                 270

Gln Glu Asn Leu Tyr Glu Arg Pro Val Asp Tyr Leu Pro Glu Arg Asp
        275                 280                 285

Val Tyr Glu Ser Leu Cys Arg Gly Glu Gly Ile Lys Met Thr Pro Arg
    290                 295                 300

Arg Gln Lys Arg Leu Phe Cys Arg Tyr His His Gly Asn Arg Val Pro
305                 310                 315                 320

Gln Leu Leu Ile Ala Pro Phe Lys Glu Glu Asp Glu Trp Asp Ser Pro
                325                 330                 335

His Ile Val Arg Tyr Tyr Asp Val Met Ser Asp Glu Glu Ile Glu Arg
            340                 345                 350

Ile Lys Glu Ile Ala Lys Pro Lys Leu Ala Arg Ala Thr Val Arg Asp
        355                 360                 365

Pro Lys Thr Gly Val Leu Thr Val Ala Ser Tyr Arg Val Ser Lys Ser
    370                 375                 380

Ser Trp Leu Glu Glu Asp Asp Asp Pro Val Val Ala Arg Val Asn Arg
385                 390                 395                 400

Arg Met Gln His Ile Thr Gly Leu Thr Val Lys Thr Ala Glu Leu Leu
```

```
                    405                 410                 415
Gln Val Ala Asn Tyr Gly Met Gly Gly Gln Tyr Glu Pro His Phe Asp
            420                 425                 430

Phe Ser Arg Ser Asp Glu Arg Asp Ala Phe Lys Arg Leu Gly Thr Gly
        435                 440                 445

Asn Arg Val Ala Thr Phe Leu Asn Tyr Met Ser Asp Val Glu Ala Gly
        450                 455                 460

Gly Ala Thr Val Phe Pro Asp Leu Gly Ala Ala Ile Trp Pro Lys Lys
465                 470                 475                 480

Gly Thr Ala Val Phe Trp Tyr Asn Leu Leu Arg Ser Gly Glu Gly Asp
                485                 490                 495

Tyr Arg Thr Arg His Ala Ala Cys Pro Val Leu Val Gly Cys Lys Trp
            500                 505                 510

Val Ser Asn Lys Trp Phe His Glu Arg Gly Gln Glu Phe Leu Arg Pro
        515                 520                 525

Cys Gly Thr Thr Glu Val Asp
        530                 535

<210> SEQ ID NO 8
<211> LENGTH: 2316
<212> TYPE: DNA
<213> ORGANISM: Rattus norvegicus

<400> SEQUENCE: 8
gcgggaggtg gggatcgtgg cggaggctca agcaggcgga gcttctgacg agggcggagc     60
cgagagcgcc cgggcgacgc cgcgggaggt tctggaaacg ccggctgctg cgcgtgtcca    120
gtttcagaga ccggtggcga ttggctgact gattcaacaa atagagcatt ctctgtgcct    180
ggagactttc aaggacggag gcaggcagaa gggaagactc agaaagtccg tgtccagagc    240
accggcaagg tcccgccctt ccagtcatg aagctccagg tgttggtgtt gctgatgtcc    300
tggtttggtg tcctgagctg ggtgcaggcg gaattcttca cctccattgg gcacatgacc    360
gacctgattt atgcagagaa ggaccctcgtc cagtctctga aggagtacat cctggcagag    420
gaagccaagc tctccaagat taagagctgg gccagtaaga tggaggccct gaccagcaag    480
tcagctgctg accccgaggg ctacctggcc catcctgtga acgcctataa gctggtgaag    540
cgattgaaca cagactggcc tgccctgggg gaccttgtcc tccaggacgc ggctgcaggt    600
tttgtggcta acctctcagt tcagcggcag ttcttcccca ctgacgagga cgagtctgga    660
gctgccagag ccctgatgcg acttcaggac acctacaaac tggatccgga catgatttct    720 agagggagc ttccaggaac aaagtaccag gccatgctga gtgtggatga ctgctttggg    780
atgggccgct cagcttacaa cgaaggagac tattaccaca ccgtgttgtg atggagcag    840 gtgctgaagc agctggatgc tggggaggag gccactgtta ccaaatccct ggtgctggac    900
tacctgagct atgccgtctt ccagctgggt gacctgcacc gtgcggtgga actcacccgt    960
cgcctgctct ctcttgaccc gagccatgaa cgagccggag ggaacctgcg gtactttgag   1020
cggctgttag aggaagaaag aggaaaatca ttgtcgaatc agacggacgc tggactagca   1080
tcgcaggaaa acttgtacga gaggcctgta gactacctgc ccgagaggga cgtgtatgag   1140
agcctgtgtc gaggggaggg catcaaaatg acacccccgga ggcagaagag cttttctgt   1200 agataccacc atggaaacag agtgccacag ctcctcattg ccccttcaa agaggaagac   1260 gagtgggaca gccacacacat cgtcaggtac tatgatgtga gtcgacgca agagatcgag   1320 aggatcaagg agattgctaa gcccaaactc gcacgagcca ctgtgcgtga tcccaagaca   1380
```

-continued

```
ggtgtcctca ctgttgctag ctacagagtt tccaaaagct cctggctaga ggaagacgat    1440
gaccctgttg tggcccgagt caaccgcagg atgcagcaca tcacagggct gacggtgaag    1500
actgcagagc tattgcaggt cgcaaactac ggaatggggg acagtacga accacacttt    1560 gacttctcga ggagcgatga gcgagatgct ttcaagcgtt tagggactgg gaaccgtgtg    1620
gccacatttc taaactacat gagtgatgtt gaagctggtg gcgccactgt cttccccgac    1680
ttgggagctg cgatttggcc caagaagggc acggctgtat tttggtataa ccttcttcgg    1740
agcggggaag gcgattatcg aacgaggcac gcggcctgcc ctgtgcttgt gggctgcaag    1800
tgggtctcca ataagtggtt ccatgagcga ggacaggagt tcttgaggcc ttgtgggaca    1860
acggaagtcg attgacgtcc ttttctgctc tgcccctccc tgtcccacag tccaaatcat    1920
cttcaagttc agtgtgacag cttcctttgt atgtcccagc tcctgtcaag caggccattg    1980
ggggagccag tgtttgtctg aattgagaga gtgtgtcctg agccgagtcc tgggtgacct    2040
gggccgcagg ctctggccag cctatgcctg ccctggctcc cagggtagtc ttgtcatggc    2100
tgtagtagag ccagactgta gcacccagca cggtgccttt gtacctcaga tatttcaggt    2160
ggacgatgtt tcagtgaaac caagttctg acactgttta catgtttgtt ttctatgaca    2220
tttctatttg ttgtggcttt aaccaaaaaa taaaataaaa caaacaaaa caaaataaaa    2280 tgttcctgcc agaagcctta aagagcttta cttcgg                              2316
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
gtacagccag catacgcca                                                   19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
agactgggac gccaaggta                                                   19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
tgtgaggaac ttgagatct                                                   19

<210> SEQ ID NO 12
<211> LENGTH: 741
<212> TYPE: PRT
<213> ORGANISM: Mus musculus

<400> SEQUENCE: 12

Met Ala Pro Arg Lys Asn Ala Lys Gly Gly Gly Gly Asn Ser Ser Ser

-continued

```
1               5                   10                  15
Ser Gly Ser Gly Ser Gly Ser Gly Ser Pro Ser Thr Gly Ser
                20                  25              30

Ser Gly Ser Ser Ser Pro Gly Ala Arg Arg Glu Ala Lys His Gly
            35              40                  45

Gly His Lys Asn Gly Arg Arg Gly Gly Ile Ser Gly Gly Ser Phe Phe
        50                  55              60

Thr Trp Phe Met Val Ile Ala Leu Leu Gly Val Trp Thr Ser Val Ala
65                      70                  75                  80

Val Val Trp Phe Asp Leu Val Asp Tyr Glu Glu Val Leu Gly Lys Leu
                85                  90                  95

Gly Val Tyr Asp Ala Asp Gly Asp Phe Asp Val Asp Ala
                100             105             110

Lys Val Leu Leu Gly Leu Lys Glu Arg Ser Pro Ser Glu Arg Thr Phe
            115             120             125

Pro Pro Glu Glu Glu Ala Glu Thr His Ala Glu Leu Glu Glu Gln Ala
        130             135             140

Pro Glu Gly Ala Asp Ile Gln Asn Val Glu Asp Glu Val Lys Glu Gln
145             150             155             160

Ile Gln Ser Leu Leu Gln Glu Ser Val His Thr Asp His Asp Leu Glu
            165             170             175

Ala Asp Gly Leu Ala Gly Glu Pro Gln Pro Glu Val Glu Asp Phe Leu
        180             185             190

Thr Val Thr Asp Ser Asp Asp Arg Phe Glu Asp Leu Pro Gly Thr
                195             200             205

Val His Glu Glu Ile Glu Asp Thr Tyr His Val Glu Asp Thr Ala Ser
        210             215             220

Gln Asn His Pro Asn Asp Met Glu Glu Met Thr Asn Glu Gln Glu Asn
225             230             235             240

Ser Asp Pro Ser Glu Ala Val Thr Asp Ala Gly Val Leu Leu Pro His
            245             250             255

Ala Glu Glu Val Arg His Gln Asp Tyr Asp Glu Pro Val Tyr Glu Pro
        260             265             270

Ser Glu His Glu Gly Val Ala Ile Ser Asp Asn Thr Ile Asp Asp Ser
        275             280             285

Ser Ile Ile Ser Glu Glu Ile Asn Val Ala Ser Val Glu Glu Gln Gln
        290             295             300

Asp Thr Pro Pro Val Lys Lys Lys Pro Lys Leu Leu Asn Lys Phe
305             310             315             320

Asp Lys Thr Ile Lys Ala Glu Leu Asp Ala Ala Glu Lys Leu Arg Lys
            325             330             335

Arg Gly Lys Ile Glu Glu Ala Val Asn Ala Phe Glu Glu Leu Val Arg
            340             345             350

Lys Tyr Pro Gln Ser Pro Arg Ala Arg Tyr Gly Lys Ala Gln Cys Glu
            355             360             365

Asp Asp Leu Ala Glu Lys Gln Arg Ser Asn Glu Val Leu Arg Arg Ala
        370             375             380

Ile Glu Thr Tyr Gln Glu Ala Ala Asp Leu Pro Asp Ala Pro Thr Asp
385             390             395             400

Leu Val Lys Leu Ser Leu Lys Arg Arg Ser Glu Arg Gln Gln Phe Leu
            405             410             415

Gly His Met Arg Gly Ser Leu Leu Thr Leu Gln Arg Leu Val Gln Leu
        420             425             430
```

```
Phe Pro Ser Asp Thr Thr Leu Lys Asn Asp Leu Gly Val Gly Tyr Leu
        435                 440                 445

Leu Leu Gly Asp Asn Asp Ser Ala Lys Lys Val Tyr Glu Glu Val Leu
    450                 455                 460

Asn Val Thr Pro Asn Asp Gly Phe Ala Lys Val His Tyr Gly Phe Ile
465                 470                 475                 480

Leu Lys Ala Gln Asn Lys Ile Ser Glu Ser Ile Pro Tyr Leu Lys Glu
                485                 490                 495

Gly Ile Glu Ser Gly Asp Pro Gly Thr Asp Asp Gly Arg Phe Tyr Phe
            500                 505                 510

His Leu Gly Asp Ala Met Gln Arg Val Gly Asn Lys Glu Ala Tyr Lys
        515                 520                 525

Trp Tyr Glu Leu Gly His Lys Arg Gly His Phe Ala Ser Val Trp Gln
    530                 535                 540

Arg Ser Leu Tyr Asn Val Asn Gly Leu Lys Ala Gln Pro Trp Trp Thr
545                 550                 555                 560

Pro Arg Glu Thr Gly Tyr Thr Glu Leu Val Lys Ser Leu Glu Arg Asn
                565                 570                 575

Trp Lys Leu Ile Arg Asp Glu Gly Leu Met Val Met Asp Lys Ala Lys
            580                 585                 590

Gly Leu Phe Leu Pro Glu Asp Glu Asn Leu Arg Glu Lys Gly Asp Trp
        595                 600                 605

Ser Gln Phe Thr Leu Trp Gln Gln Gly Arg Lys Asn Glu Asn Ala Cys
    610                 615                 620

Lys Gly Ala Pro Lys Thr Cys Ala Leu Leu Glu Lys Phe Ser Glu Thr
625                 630                 635                 640

Thr Gly Cys Arg Arg Gly Gln Ile Lys Tyr Ser Ile Met His Pro Gly
                645                 650                 655

Thr His Val Trp Pro His Thr Gly Pro Thr Asn Cys Arg Leu Arg Met
            660                 665                 670

His Leu Gly Leu Val Ile Pro Lys Glu Gly Cys Lys Ile Arg Cys Ala
        675                 680                 685

Asn Glu Thr Arg Thr Trp Glu Glu Gly Lys Val Leu Ile Phe Asp Asp
690                 695                 700

Ser Phe Glu His Glu Val Trp Gln Asp Ala Ser Ser Phe Arg Leu Ile
705                 710                 715                 720

Phe Ile Val Asp Val Trp His Pro Glu Leu Thr Pro Gln Gln Arg Arg
                725                 730                 735

Ser Leu Pro Ala Ile
            740

<210> SEQ ID NO 13
<211> LENGTH: 6652
<212> TYPE: DNA
<213> ORGANISM: Mus musculus

<400> SEQUENCE: 13
gccgaggccg gggggagctg agcgctcttg gcagcctaag gagtcgcagg ctgggcgcac      60
gcgaggctaa ccgcgcggct gcacgctggt gcaagtcgtc cgaggcgcag cgagcgcagt     120
ggacgctaag gcgctgctac aggagtctcg aagcccggt gtccctagtg cactcagcaa     180
ggccccggtt ctctgcagtc cccggagcag ctcgcgatgg ccccgcgcaa gaacgccaag     240
ggcggcggcg gcaacagcag cagcagcggc agcggcagcg gctcgggcag cggtagcccg     300
agcacgggta gcagcggtag cagcagtagc cccggggctc ggagagaggc aaagcacgga     360
```

```
ggacacaaga atgggagaag aggagggatt tcaggagggt ccttttcac atggttcatg      420 gtcattgcat tgctcggcgt ctggacatct gtggctgtcg tgtggtttga cttggtcgat      480
tatgaagaag ttctaggaaa actaggagtc tatgatgcgg atggcgatgg agactttgat      540
gtggatgatg ccaaagtttt attaggcctt aaagaaagat ctccttctga gaggacattt      600
ccaccggagg aggaggcaga gactcacgct gagctggagg agcaggcccc tgaggggca       660 gacatccaga atgttgaaga tgaagtaaag aacaaattc agtcccttct tcaggaatca       720
gtacacacag accatgacct tgaagcagat gggctggcag agaaccaca gccggaggtt       780 gaggacttcc tcacagtgac cgacagtgat gacagatttg aggacctgga acccgggaca      840
gttcatgaag aaatcgagga tacttaccat gtggaagaca cagcatcgca gaaccatcca      900
aatgacatgg aagagatgac gaatgagcag gaaaattcag atcccagtga agcagtgaca      960
gatgcaggtg tgctgctgcc ccatgcagag gaagtaagac accaagacta tgatgaacca     1020
gtatatgaac cctcagagca tgaaggggtc gcgatttcag ataacaccat agatgattcc     1080
agcataatct cagaagaaat aaatgtcgcc tctgttgaag aacagcaaga cacaccacca     1140
gttaagaaga gaagcctaa  acttctgaac aaatttgata agacaattaa ggctgagctg     1200
gatgctgcag aaaagctccg gaaaagggggt aaaattgagg aagcagtgaa cgcatttgaa     1260
gaactggttc gaaagtaccc tcagagccca cgagcaagat atggcaaagc gcagtgtgaa     1320
gatgacttgg cagagaagca gagaagcaat gaggttctgc gcagggccat cgagacctac     1380
caggaggcag ccgacctgcc tgatgcccct acagacctgg tgaagctgag cttgaagcga     1440
aggtcggaac ggcagcagtt tctaggtcac atgagaggtt ctctacttac cctccagaga     1500
ctagttcaac tgttccctag tgatactacc ttaaaaaacg accttggcgt aggatacctc     1560
ttgttgggag acaacgacag tgccaagaag gtttacgaag aggtgctaaa tgtgacacca     1620
aatgatggct tcgctaaagt gcattacggc ttcatcctga aggcacagaa caagatatct     1680
gagagcattc cctacttaaa ggaaggaatc gaatctgggg accctggcac ggatgatggc     1740
cggttttact ccacttgggg ggatgccatg cagagggtcg ggaacaaaga ggcatataag     1800
tggtatgaac ttgggcacaa gagaggacat tttgcctctg tctggcagcg ttccctctac     1860
aatgtgaatg gtctgaaggc tcagccgtgg tggacaccca gggagactgg ctacacagag     1920
ctagtgaagt ctttagagag aaactggaag ttaatccgtg atgaaggcct catggtgatg     1980
gataaagcca agggtctctt cctgcctgag gacgaaaacc ttcgggagaa gggcgactgg     2040
agccagttca cactgtggca gcaaggaagg aagaatgaga atgcctgtaa aggagcgcct     2100
aagacctgtg ctttactaga aaagttttcc gaaacaacag gatgcagaag aggacagatc     2160
aaatactcca tcatgcaccc tggaactcat gtgtggccgc atacaggacc cacaaactgc     2220
aggctccgaa tgcatctggg gttagtgatc cccaaggaag gctgcaagat ccggtgtgcc     2280
aatgagacca ggacgtggga agaaggcaag gtgctcatct tgatgactc ttttgagcac     2340 gaggtttggc aggatgcctc gtctttccgg ctgatattca tcgtggatgt gtggcacccc     2400
gagctgaccc ctcagcagag acgcagcctt cccgcaattt gaaaggcact gacgcagact     2460
tggttgctct ccagggaggc tgcctttctg gttccttttg ggtgtggaga tagaagtcca     2520
agtaccatga ctcttcatcc ccgtgccatg cagctggaga cctctcaaggt tccttctgga     2580 ttagaactca ctgagggaa  catttgcctt cctgcgattc atttaggagg cctcttgctt     2640
catgtcaccc atgacagcac agaactagtg cctgcattta aggggcagaa aacttggttg     2700
tgttgtctac atggctggcc aaagatattt ttctacatag aatagtgtct acatcaatgc     2760
```

```
acatggagga tatactatat agagaaactg tgaatgaatc actttagttt gtaattttc      2820
tatgcagtta tattttttcta agtagctaaa ctgttctgtc accatctacc cccatgtttt    2880
cgttgacttt aatgacaaga agtataaatt ctttacgtct gttaaatagt aattttcctg    2940
gtaaattcag acatttcttt ttttagaaag aaaaaaatca cgtgtgaaag aaaagaactt    3000
tgttttccta acataaattg gaagtcatgc taggatgcat gaactgtgcc aacacttgcc    3060
cttgggtcta cctgtgtatc ctcatttaga ctcagtgtct ccccctttct ctgtgctaat    3120
agtacaaagt tgttatttct aagagcaaca tttcttttta aattacactg agcaaagcca    3180
tagaaacatt ttatgtgata ggaaaatacc acagataatg gagcttggag agaaaatatc    3240
acatggaagt gaaatttcct gctcagggtc agggacccag gtagcctggc ctctttgcct    3300
tctatacccca aggcctggag tctgcagttc ctgcctgctg tagatccact tacgtgtcaa    3360
aaagaaggcc tcttagtctc tgagagtctc ttcactattt tatccatgta ggaatagcag    3420
catagaaagt gcccagggat gctagcatcc taggtggtca agcatccttg attatgaatt    3480
tgcagtgctt ttccatcttc ctcccctcag aataatgtca gccatctcat tttatactga    3540
accagcgttg acaggcatgt ttgatttgag tgctatccat ggctgagaaa gagcagtaga    3600
aagccatctt gctcctcaag atgatcatta gtaaagcatt gctgcatttt attttctatt    3660
ttaaaattaa agataactca agccctagaa tgtaatgaca ttcatgcact gatctctaag    3720
ccagtcgaac aacattgctg cagaaatggc tggtattcca gccacacaga gatgtgtgcc    3780
tttcaagcag tgcccaaaaa aagcagcttt ctgtacctca tttaaagagc aattcattga    3840
gcttgatcct ttcccttta gcttaaggac attagctctt cgtaggaaag tttacaaaat    3900
atgtgtccat tcttaaaata ggtacttgtc ccttcctttg ccagtgttca aaaattcctc    3960
taaaacagat ggcaaaggca tgaggggaaa tatcaaatcc ttaccaaatt ccagaaaaga    4020
aaacaaactc tcagacaaca gaaagttatt tgtgttcttc agtatttatt aaacagagga    4080
acttactgac aaaggcaata caatccagtg ttcatgtagt aaccctcggt tacctgctgg    4140
gtttagttct cctctatact acatatacat agcgaaatgc aaaccatgtg ttctcattgt    4200
taaactatca ccttacatcc atggaataaa atggaggaaa tgagtgaaaa ttagctgtta    4260
acttagtaaa tataacatgt ttttaaaat atggtcatta cagtaggatt ctaaatcttg    4320
ccttgtgaaa agccagcagt accgttactt ttgcaagtgt tggcagtggt gcactccaac    4380
agcattttaa gtacttggat cccacgttga tcttataaac acaagcaata aaagattttc    4440
taattcactt taattttcc tcgctcttac ttgtgtcata agaaaagaat ttccatccat    4500
gtcttggtaa acattttca aggttattat tttacaattc taaaggtcta tacaaaatga    4560
attggtaggg tttttttttt aatatactat gatgcaattg tttgggaaat attttaaaat    4620
tctgtttcaa ttttgcttct tcaaggttgg aacataaaaa tagcttctgt tactattctc    4680
tgccagtaga aaaaaataat aaaacagtag atcaactgag gagtatacat ctagtttgta    4740
gctcagggct cagggggttag gccctggggtt tgatcttcag cattggaggg agacagagaa    4800
gagagggtaa cagggagaca gagaaagaaa gacaaggaa aaggagagga gtgtaaggag    4860
gagagaagtg ggaaggaaca gggaaagaga gagatggaga gagggaagtg gccatagtca    4920
gtaatgtttt tgtgtttatgg cgggaagtaa gttgaattgg tttcctctctt tctttaggct    4980
gttcagctag taaatcactc taccaagtgc ttaaaatgta aagtatttta ataagtgtta    5040
gcaattaaaa attttgacat tatcactctg gtcatattag taagtgtctg tgtcgtacag    5100
atgctagaga ataaggtatc tacacatact cagctggtct caggaaacat ggcacagata    5160
```

```
aaatatcctc cccctttgctg ttctctgtct gacttcctat gcatggggc tgggatccat    5220 ttctaaggag aatggataag gaagtaggct ggtcttggc atttcatctt gcattcttgg     5280
tcctctttag cttggtactt acatgctgat ccatccttaa gggtctttct gtgagatttg    5340
aatgcctgcc ccctcagggc ctttctccac aggtaatagg agcatgggga caaagggact    5400
tatttgatag caagttttg ctgtagtaac ccaagaatta acttaaaagg gtaatcagtc     5460
accagtgtgt gtgtgtgtgt gtgtgtggtg tgtggtgtgt gttccaatga gttgccccct    5520
ctctgtaggc attcgcctac aggaaatcac tttgctacaa tgaagcagcc tcttttttt    5580 tcaaactgcc tctttgtctt aaaaagcaat tcatgaaagt cagctgatgg tctgacaagc    5640
aacacgatgt ccaaatcatt cttgtaggag agagatttaa atgaaaaact ttgcaaatag    5700
ccagacgtgg gagatcacac tcttaggctg actacttaga tgctggtgat gaggtcagga    5760
aataagtcaa taggactgga aattattgga gctactgctg ctggggttca gcactacatt    5820
aaacttgctg atgtgtctgc acattttaac tctgttttat ttatttcgga atgcatttca    5880
tcttaatttg caaaacctgg agagggttcc tgtgtgagtc tttagagtga tgtatatgca    5940
actaatttag ggttttttc cccttttgaa gtatatttgc tgccaaaaat atgaggggag    6000 aatcctttt acataaatgc ctttcttcat ccccgtcacc attcctcact aaaacataaa     6060
ttaattcgtt aaattttaa aagcgtctct cagatctttg tccggtgtgg gctacccaga     6120
ccaatggttg ctgacagtca tggctgggac tgggatggag gacctcatgt caagcagagc    6180
acacagagtg tctgtaggtc agttgcacag gcttgctgga cggttgctcc actgagatg    6240 tcacatgatg ctggctggct cagtccagag ccagcagtgg ctgggtgttc tcattttctc    6300
ctttctcttc atgtttcaag gtcccagctt ctaccacaga ctgagatcta acaagagagg    6360
aaggagacac acacagtcac agacagtcca tactggtgat gcttgctact cacctgaatc    6420
agagcatgtg aaatagctac ttagtgcttc ctttctgcca tctgttttcc acacaccact    6480
ttatttcttt tttttttttt tctttttgtt tttctgaaga ttgaatctgg tcattctgag    6540 attcttttt tttctgctg aatttgatcc atatcttttt gctgtaataa gtcctatgag    6600
tgtaacattt tgttcatgtt ccaaataaaa ataaaggtaa ttcgaaagat gc    6652
```

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgggagaaga ggaggcatt                                                  19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaggagggat ttcaggagg                                                  19

<210> SEQ ID NO 16
<211> LENGTH: 18
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 16
gaggaagtac cattatat             18

<210> SEQ ID NO 17
<211> LENGTH: 4082
<212> TYPE: DNA
<213> ORGANISM: Homo sapiens

<400> SEQUENCE: 17

```
gcgcgcgccg gcctgggcag gcgagcgggc gcgctcccgc ccctctccc ctccccgcgc    60
gcccgagcgc gcctccgccc ttgcccgccc cctgacgctg cctcagctcc tcagtgcaca   120
gtgctgcctc gtctgagggg acaggaggat caccctcttc gtcgcttcgg ccagtgtgtc   180
gggctgggcc ctgacaagcc acctgaggag aggctcggag ccgggcccgg accccggcga   240
ttgccgcccg cttctctcta gtctcacgag gggtttcccg cctcgcaccc ccacctctgg   300
acttgccttt ccttctcttc tccgcgtgtg gaggagccca gcgcttaggc cggagcgagc   360
ctggggggccg cccgccgtga agacatcgcg gggaccgatt caccatggag ggcgccggcg   420
gcgcgaacga caagaaaaag ataagttctg aacgtcgaaa agaaaagtct cgagatgcag   480
ccagatctcg gcgaagtaaa gaatctgaag ttttttatga gcttgctcat cagttgccac   540
ttccacataa tgtgagttcg catcttgata aggcctctgt gatgaggctt accatcagct   600
atttgcgtgt gaggaaactt ctggatgctg gtgatttgga tattgaagat gacatgaaag   660
cacagatgaa ttgcttttat ttgaaagcct tggatggttt tgttatggtt ctcacagatg   720
atggtgacat gatttacatt tctgataatg tgaacaaata catgggatta actcagtttg   780
aactaactgg acacagtgtg tttgatttta ctcatccatg tgaccatgag gaaatgagag   840
aaatgcttac acacagaaat ggccttgtga aaaagggtaa agaacaaaac acacagcgaa   900
gcttttttct cagaatgaag tgtaccctaa ctagccgagg aagaactatg aacataaagt   960
ctgcaacatg gaaggtattg cactgcacag gccacattca cgtatatgat accaacagta  1020
accaacctca gtgtgggtat aagaaaccac ctatgacctg cttggtgctg atttgtgaac  1080
ccattcctca cccatcaaat attgaaattc ctttagatag caagacttc ctcagtcgac  1140
acagcctgga tatgaaattt tcttattgtg atgaaagaat taccgaattg atgggatatg  1200
agccagaaga acttttaggc cgctcaattt atgaatatta tcatgctttg gactctgatc  1260
atctgaccaa aactcatcat gatatgtttt ctaaaggaca agtcaccaca ggacagtaca  1320
ggatgcttgc caaaagaggt ggatatgtct gggttgaaac tcaagcaact gtcatatata  1380
acaccaagaa ttctcaacca cagtgcattg tatgtgtgaa ttcgttgtg agtggtatta  1440
ttcagcacga cttgattttc tcccttcaac aaacagaatg tgtccttaaa ccggttgaat  1500
cttcagatat gaaaatgact cagctattca ccaaagttga atcagaagat acaagtagcc  1560
tctttgacaa acttaagaag gaacctgatg ctttaacttt gctggcccca gccgctggag  1620
acacaatcat atctttagat tttggcagca acgacacaga aactgatgac cagcaacttg  1680
aggaagtacc attatataat gatgtaatgc tcccctcacc caacgaaaaa ttacagaata  1740
taaatttggc aatgtctcca ttacccaccg ctgaaacgcc aaagccactt cgaagtagtg  1800
ctgacccctg cactcaatcaa gaagttgcat taaattaga accaaatcca gagtcactgg  1860
aactttcttt taccatgccc cagattcagg atcagacacc tagtccttcc gatggaagca  1920
```

```
ctagacaaag ttcacctgag cctaatagtc ccagtgaata ttgttttat gtggatagtg    1980
atatggtcaa tgaattcaag ttggaattgg tagaaaaact ttttgctgaa gacacagaag    2040
caaagaaccc attttctact caggacacag atttagactt ggagatgtta gctccctata    2100
tcccaatgga tgatgacttc cagttacgtt ccttcgatca gttgtcacca ttagaaagca    2160
gttccgcaag ccctgaaagc gcaagtcctc aaagcacagt tacagtattc cagcagactc    2220
aaatacaaga acctactgct aatgccacca ctaccactgc caccactgat gaattaaaaa    2280
cagtgacaaa agaccgtatg gaagacatta aaatattgat tgcatctcca tctcctaccc    2340
acatacataa agaaactact agtgccacat catcaccata tagagatact caaagtcgga    2400
cagcctcacc aaacagagca ggaaaaggag tcatagaaca gacagaaaaa tctcatccaa    2460
gaagccctaa cgtgttatct gtcgctttga gtcaaagaac tacagttcct gaggaagaac    2520
taaatccaaa gatactagct ttgcagaatc tcagagaaa gcgaaaaatg aacatgatg     2580
gttcactttt tcaagcagta ggaattggaa cattattaca gcagccagac gatcatgcag    2640
ctactacatc actttcttgg aaacgtgtaa aaggatgcaa atctagtgaa cagaatggaa    2700
tggagcaaaa gacaattatt ttaatacct ctgatttagc atgtagactg ctggggcaat    2760
caatggatga aagtggatta ccacagctga ccagttatga ttgtgaagtt aatgctccta    2820
tacaaggcag cagaaaccta ctgcagggtg aagaattact cagagctttg gatcaagtta    2880
actgagcttt ttcttaattt cattccttt tttggacact ggtggctcat tacctaaagc    2940
agtctattta tattttctac atctaatttt agaagcctgg ctacaatact gcacaaactt    3000
ggttagttca attttgatcc cctttctact taatttacat taatgctctt ttttagtatg    3060
ttctttaatg ctggatcaca gacagctcat tttctcagtt ttttggtatt taaaccattg    3120
cattgcagta gcatcatttt aaaaaatgca cctttttatt tatttatttt tggctaggga    3180
gtttatccct ttttcgaatt ttttttaaga agatgccaat ataattttg taagaaggca    3240
gtaacctttc atcatgatca taggcagttg aaaaatttt acacctttt tttcacattt     3300
tacataaata ataatgcttt gccagcagta cgtggtagcc acaattgcac aatatatttt    3360
cttaaaaaat accagcagtt actcatggaa tatattctgc gtttataaaa ctagtttta    3420
agaagaaatt ttttttggcc tatgaaattg ttaaacctgg aacatgacat tgttaatcat    3480
ataataatga ttcttaaatg ctgtatggtt tattatttaa atgggtaaag ccatttacat    3540
aatatagaaa gatatgcata tatctagaag gtatgtggca tttatttgga taaaattctc    3600
aattcagaga aatcatctga tgtttctata gtcactttgc cagctcaaaa gaaaacaata    3660
ccctatgtag ttgtggaagt ttatgctaat attgtgtaac tgatattaaa cctaaatgtt    3720
ctgcctaccc tgttggtata aagatatttt gagcagactg taaacaagaa aaaaaaaatc    3780
atgcattctt agcaaaattg cctagtatgt taatttgctc aaaatacaat gtttgatttt    3840
atgcactttg tcgctattaa catcctttt ttcatgtaga tttcaataat tgagtaattt    3900
tagaagcatt attttaggaa tatatagttg tcacagtaaa tatcttgttt tttctatgta    3960
cattgtacaa atttttcatt ccttttgctc tttgtggttg gatctaacac taactgtatt    4020
gttttgttac atcaaataaa catcttctgt ggaccaggca aaaaaaaaa aaaaaaaaa    4080
aa                                                                    4082
```

<210> SEQ ID NO 18
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 18
cggaacaggc tatgtccgt                                                  19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agactgggac gccaaggta                                                  19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtacagccag catacgcca                                                  19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
caggtgagaa aggtgtgag                                                  19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agatctcaag ttcctcaca                                                  19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgtgaggaac ttgagatct                                                  19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 24
gatcagccag catacgcca                                                19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tggcgtatgc tggcttgtac                                               20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cttcaaggac cccaagcggg ctcta                                         25

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgagtttata ctgcccagtt                                               20

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cttcaaggac cccaagcggc tctac                                         25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttcgtttca gtgccacata ccaac                                         25

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 30
tgaagtctgc tcgctatttg gta                                          23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctatggtgca tggttctgtt gtt                                          23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaagctactg ccgtccgatt gag                                          23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgctggcttt ggtgaggttt gat                                          23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaattcgaca tgatccaggg act                                          23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgcacttaca cgacttcacc acc                                          23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
```

```
atggctcaga gcaacaagtt caa                                           23
```

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
gacaaaggct gtggaggaag acg                                           23
```

SHRNA GENE THERAPY FOR TREATMENT OF ISCHEMIC HEART DISEASE

STATEMENT REGARDING FEDERALLY SPONSORED RESEARCH OR DEVELOPMENT

This invention was made with Government support under contracts HL089027 and HL074883 awarded by the National Institutes of Health. The Government has certain rights in this invention.

BACKGROUND OF THE INVENTION

1. Field of the Invention

This invention is in the fields of treatment for cardiac disease, treatment of ulcers, gene therapy and molecular imaging.

2. Background of the Invention

Coronary artery disease is the leading cause of morbidity and mortality in the Western world.[1] Conventional treatment for coronary artery disease consists of medical therapy as the first-line strategy followed by percutaneous coronary intervention or coronary artery bypass graft. However, a significant number of patients will still have refractory angina despite these treatments.[2] For such patients, the alternative approach of delivering potent angiogenic factors to stimulate new vessel growth has undergone intense investigation over the past decade.

Current methods of gene therapy approaches for treatment of cardiovascular disease rely on single therapeutic genes such as vascular endothelial growth factor (VEGF) or fibroblast growth factor (FGF). With the use of various gene transfer techniques, it is now possible to modify cardiac cells to overexpress beneficial proteins or inhibit pathological proteins and achieve desired therapeutic effects.[3] The field has expanded tremendously from preclinical studies in the early 1990s to large randomized clinical trials in the early 2000s. Although initial Phase 1 trials in patients with myocardial ischemia provided encouraging results, recent Phase 2 randomized trials (AGENT, VIVA, KAT) yielded only modest benefits.[4-6] These inconsistencies have been attributed to the unclear role of single therapeutic genes such as vascular endothelial growth factor or fibroblast growth factor as well as the inability to monitor gene transfer in vivo.[7]

During hypoxia, upregulation of hypoxia inducible factor-1 α (HIF-1α) transcriptional factor can activate several downstream angiogenic genes. However, HIF-1α is naturally degraded by prolyl 4-hydroxylase-2 (HIF-PHD2) protein.

The prolyl 4-hydroxylases (PH4s) catalyze the formation of 4-hydroxyproline by the hydroxylation of proline residues in peptide linkages. The P4Hs hydroxylating the hypoxia-inducible factor are cytoplasmic and nuclear enzymes that play a key role in the response of calls to hypoxia.[27] Three prolyl hydroxylase isoforms have been identified and use $O_2$ and 2-oxyglutarate as substrates to generate 4-hydroxyproline at residue 402 and/or 564 of HIF-1α[14]

The Homo Sapien (human) protein and nucleotide sequences of HIF-PHD2 has been determined and is publicly available through many on-line databases, such as, for example, NCBI (available at www.ncbi.nlm.nih.gov).

There are three human transcript variants for HIF-PHD2. The accession number for transcript variant 1 is (NM_177939). The amino sequence is set forth in SEQ ID NO: 1 and the nucleotide sequence is set forth in SEQ ID NO: 2. The accession number for transcript variant 2 is (NM001017962). The amino acid sequence is set forth in SEQ ID NO: 3 and the nucleotide sequence is set forth in SEQ ID NO: 4. The accession number for transcript variant 3 is (NM004199). The amino acid sequence is set forth in SEQ ID NO: 5 and the nucleotide sequence is set forth in SEQ ID NO: 6.

The rat HIF-PHD2 protein sequence and nucleotide sequence are found at accession number NM001108275. The amino acid sequence is set forth in SEQ ID NO: 7 and the nucleotide sequence is set forth in SEQ ID NO: 8.

The accession number for asparaginyl hydroxylase ("ASPHD" or "ASPH") is NM_023066. The amino acid sequence is set forth in SEQ ID NO: 12 and the nucleotide sequence is set forth in SEQ ID NO: 13.[30]

Newer approaches based on the upstream transcriptional factor HIF-1α may be a more natural choice. HIF-1α is known to control the expression of over 60 genes that affect cell survival and metabolism in adverse conditions, including vascular endothelial growth factor, fibroblast growth factor, insulin-like growth factor, erythropoietin, and nitric oxide synthase among others.[3] Unfortunately, HIF-1α has a biological half-life of only approximately 5 minutes under normoxic condition.[8] This is because during normoxic condition, HIF-1α is hydroxylated by oxygen-dependent prolyl 4-hydroxylase-2 (PHD2), ubiquitinated, and subsequently degraded.

Thus, a need still exists for a method of treating a vascular disease or disorder in a mammal. In particular, there exists a need to treat cardiovascular diseases, in particular ischemic heart disease and peripheral vascular disease by gene therapy. A need also exists for treatment of decubitis ulcers. A means of monitoring the gene transfer and expression in vivo of the vectors used in the treatment of cardiac diseases, such as for example, ischemic heart disease and peripheral vascular disease, is needed as is a means for monitoring treatment of decubitis ulcers. Further, a need remains for vectors capable of expressing therapeutic agents, such as shRNA molecules, for extended periods of time.

SUMMARY OF THE INVENTION

Accordingly, the present invention includes a method of treating diseases, such as ischemic heart diseases and peripheral vascular disease, in a subject in need thereof by shRNA gene therapy. The invention also includes a method of treating decubitis ulcers. The invention further includes a method of treating cardiac disease, ischemic heart disease, vascular peripheral disease, and decubitis ulcers by modulating any of the HIF-1α pathway, the HIF-PHD2 pathway and the ASPDH pathway. The present invention also provides a means for monitoring gene transfer and expression of the HIF-PHD2, HIF-1α and ASPDH vectors in vivo. The present invention includes novel shRNA vectors for use in the method of treating cardiac disease, ischemic heart disease, vascular peripheral disease, decubitis ulcer and the vectors in a pharmaceutically acceptable composition.

DETAILED DESCRIPTION OF THE INVENTION

Applicants demonstrate herein that the inhibition of HIF-1α degradation through short hairpin RNA (shRNA) knockdown of PHD2 in the ischemic heart represents a novel angiogenic therapy approach. At the same time, Applicants tracked the shRNA vector expression in vivo noninvasively through novel molecular imaging technology. Applicants also demonstrate herein knockdown of the ASPH gene.

The invention includes a method of treating ischemic heart disease in a mammal comprising administering to heart tissue of the mammal in need of treatment an effective amount of a vector in a pharmaceutically acceptable carrier, the vector comprising, in operable linkage i) a promoter; ii) a polynucleotide encoding a small hairpin RNA (shRNA), the polynucleotide comprising a sense nucleotide sequence which corresponds to a nucleotide sequence in a mRNA transcript of hypoxia inducible factor-1 α (HIF-1α) prolyl-4-hydroxylase protein [HIF-PHD2] and a nucleotide sequence which is complementary to the sense nucleotide sequence; wherein upon expression of the vector, neo-angiogenesis is induced in the heart tissue, thereby treating the mammal's ischemic heart disease. In one aspect, the sense nucleotide sequence is the nucleotide sequence 5'-GTACAGCCAGCATACGCC-3' (nucleotides 1-18 of SEQ ID NO: 9) or the sense nucleotide sequence is the nucleotide sequence 5'-AGACTGGGACGCCAAGGTA-3' (SEQ ID NO: 10). In another aspect, the vector further comprises, in operable linkage, a promoter, an HIF-1 α responsive element and a reporter gene. In a different aspect, the HIF-1α responsive element is one or more copies of a hypoxia response element (HRE). In some instances, the HIF-1α responsive element comprises five copies of the HRE element. The reporter gene is a firefly luciferase (Fluc) gene. In other aspects, the method further comprises monitoring the mammal for accumulation of HIF-1α by detecting the presence or absence of a detectable signal from the reporter gene. In some instances, the vector or vectors is(are) readministered to the mammal after a predetermined period of time. The mammal may be a human. In other aspects, the vector comprises more than one polynucleotide. Each polynucleotide may encode a different shRNA. Each polynucleotide may encode an shRNA which is the same as, or different from, another shRNA in the vector. Each vector can comprise more than polynucleotide.

The invention includes at least one vector. The vector comprises a) a promoter; b) at least one polynucleotide, the polynucleotide encoding a small hairpin RNA (shRNA), the polynucleotide comprising a sense nucleotide sequence which corresponds to a nucleotide sequence in a mRNA transcript and a nucleotide sequence which is complementary to said sense nucleotide sequence; c) a promoter, an HIF-1α responsive element and a reporter gene in operable linkage; and, wherein the mRNA transcript is selected from the group consisting of HIF-1α mRNA, ASPH mRNA, HIF-PHD2 mRNA and any combination thereof. In some instances, the sense polynucleotide has the sequence 5'-GTACAGCCAGCATACGCCA-3' (SEQ ID NO: 9) or 5'-AGACTGGGACGCCAAGGTA-3' (SEQ ID NO: 10). In some instances, the sense polynucleotide has the sequence (shAsphd-3) 5'-TGGGAGAAGAGGAGGCATT-3' (SEQ ID NO: 14) or (shAsphd-4) 5'-GAGGAGGGATTTCAGGAGG-3' (SEQ ID NO: 15). In some aspects, the sense polynucleotide has the sequence (HIF-1α) 5'-GAGGAAGTACCATTATAT-3' (SEQ ID NO: 16). In other aspects, the vector comprises one or more of SEQ ID Nos: 9, 10, 14, 15 or 16 but does not comprise an HIF-1α element. The invention includes vectors in pharmaceutically acceptable compositions. In the vector, the HIF-1α responsive element is one or more copies of a hypoxia response element (HRE). In one aspect, the HIF-1α responsive element comprises five copies of the HRE element.

The invention also includes a method of treating a disease or disorder in a mammal by knocking down hypoxia inducible factor-1 α (HIF-1 α) prolyl-4-hydroxylase [HIF-PHD2] comprising administering to the mammal in need of treatment an effective amount of a vector in a pharmaceutically acceptable carrier, the vector comprising, in operable linkage: i) a promoter; ii) a polynucleotide encoding a small hairpin RNA (shRNA), the polynucleotide comprising a sense nucleotide sequence which corresponds to a nucleotide sequence in a mRNA transcript of hypoxia inducible factor-1 α (HIF-1 α) prolyl-4-hydroxylase protein [HIF-PHD2] and a nucleotide sequence which is complementary to the sense nucleotide sequence; iii) a promoter, an HIF-1α responsive element, and a reporter gene in operable linkage; wherein upon expression of the vector, expression of HIF-PHD2 is knocked down, thereby treating the mammal's disease or disorder. The disease or disorder is selected is selected from the group consisting of ischemic heart disease, peripheral vascular disease and decubitis ulcer. In some instances the sense nucleotide sequence is the nucleotide sequence 5'-GTACAGCCAGCATACGCCA-3' (SEQ ID NO: 9). In other aspects, the sense nucleotide sequence is the nucleotide sequence 5'-AGACTGGGACGCCAAGGTA-3' (SEQ ID NO: 10). The HIF-1α responsive element may be one or more copies of a hypoxia response element (HRE). In one aspect, the HIF-1α responsive element comprises five copies of the HRE element. The reporter gene may be a firefly luciferase (Fluc) gene. The method of the invention further comprises monitoring the mammal for accumulation of HIF-1α by detecting the presence or absence of a detectable signal from the reporter gene. In some instances the mammal is a human. In some treatments, the vector is readministered to the mammal after a predetermined period of time. In the method, the vector can comprise more than one polynucleotide. Each polynucleotide encodes an shRNA selected from the group consisting of HIF-1α shRNA, ASPH shRNA and HIF-PHD2 shRNA. The vector can comprise any polynucleotide combination thereof.

Definitions

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "complementary nucleotide sequence," also known as an "antisense sequence," refers to a sequence of a nucleic acid that is completely complementary to the sequence of a "sense" nucleic acid encoding a protein (e.g., complementary to the coding strand of a double-stranded cDNA molecule or complementary to an mRNA sequence). Herein, nucleic acid molecules are provided that comprise a sequence complementary to at least about 15, 16, 17, 18, 19, 20, 21, 22, 23, 24, or 25 nucleotides or an entire gene coding strand, or to only a portion thereof.

As used herein, the term "correspond to a nucleotide sequence" refers to a nucleotide sequence of a nucleic acid encoding an identical sequence. In some instances, when antisense nucleotides (nucleic acids) or siRNA's (small inhibitory RNA) bind to a target sequence a particular antisense or small inhibitory RNA (siRNA) sequence is substantially complementary to the target sequence, and thus will specifically bind to a portion of an mRNA encoding polypeptide. As such, typically the sequences of those nucleic acids will be highly complementary to the mRNA target sequence, and will have no more than 1, 2, 3, 4, 5, 6, 7, 8, 9, or 10 base mismatches throughout the sequence. In many instances, it may be desirable for the sequences of the nucleic acids to be exact matches, i.e. be completely complementary to the sequence to which the oligonucleotide specifically binds, and therefore have zero mismatches along the complementary stretch. Highly complementary sequences will typically bind quite specifically to the target sequence region of the mRNA and will therefore be highly efficient in reducing, and/or even inhibiting the translation of the target mRNA sequence into polypeptide product. See, for example, U.S. Pat. No. 7,416,849.

Substantially complementary oligonucleotide sequences will be greater than about 80 percent complementary (or '% exact-match') to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to the target mRNA to which the designed oligonucleotide specifically binds. See, for example, U.S. Pat. No. 7,416,849. Percent similarity or percent complementary of any nucleic acid sequence may be determined, for example, by utilizing any computer programs known in the art.

As used herein, the term "decubitis ulcer (pressure ulcer)" refers to an area of skin that breaks down due to constant pressure against the skin. The constant pressure reduces the blood supply to that area, and the affected tissue dies. A pressure ulcer starts as reddened skin but gets progressively worse, forming a blister, then an open sore, and finally a crater.[28]

As used herein, the term "knock-down" or "knock-down technology" refers to a technique of gene silencing in which the expression of a target gene or gene of interest is reduced as compared to the gene expression prior to the introduction of the siRNA, which can lead to the inhibition of production of the target gene product. "Double knockdown" is the knockdown of two genes. The term "reduced" is used herein to indicate that the target gene expression is lowered by 0.1-100%. For example, the expression may be reduced by 0.5, 1, 5, 10, 15, 20, 25, 30, 35, 40, 45, 50, 55, 60, 65, 70, 75, 80, 85, 90, 95, or even 99%. The expression may be reduced by any amount (%) within those intervals, such as for example, 2-4, 11-14, 16-19, 21-24, 26-29, 31-34, 36-39, 41-44, 46-49, 51-54, 56-59, 61-64, 66-69, 71-74, 76-79, 81-84, 86-89, 91-94, 96, 97, 98 or 99. Knock-down of gene expression can be directed by the use of siRNAs or shRNAs. For example, RNA interference (RNAi), which can involve the use of siRNA, has been successfully applied to knockdown the expression of specific genes in plants, *D. melanogaster, C. elegans, trypanosomes, planaria, hydra*, and several vertebrate species including the mouse and zebrafish. See, for example, U.S. Pat. No. 7,416,849.

As used herein, the term "neo-angiogenesis" refers to the growth of new blood vessels from pre-existing blood vessels.

As used herein, the term "nucleotide sequence" refers to a polymer of DNA or RNA which can be single-stranded or double-stranded, optionally containing synthetic, non-natural or altered nucleotide bases capable of incorporation into DNA or RNA polymers. The term "polynucleotide" is used interchangeably with the term "oligonucleotide." The term "nucleotide sequence" is interchangeable with "nucleic acid sequence" unless otherwise clearly stated. "Nucleotide sequence" and "nucleic acid sequence" are terms referring to a sequence of nucleotides in a polynucleotide molecule.

As used herein, the term "operably-linked" refers to the association of nucleic acid sequences on a polynucleotide so that the function of one of the sequences is affected by another. For example, a regulatory DNA sequence is said to be "operably linked to" a DNA sequence that codes for an RNA ("an RNA coding sequence" or "shRNA encoding sequence") or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. An RNA coding sequence refers to a nucleic acid that can serve as a template for synthesis of an RNA molecule such as an siRNA and an shRNA. Preferably, the RNA coding region is a DNA sequence.

As used herein, the term "peripheral vascular disease" refers to any disease or disorder of the circulatory system outside of the brain and heart. Although the term peripheral vascular disease can include any disorder that affects any of the blood vessels, it often is used as a synonym for peripheral artery disease. Peripheral vascular disease is the most common disease of the arteries. It is caused by build-up of fatty material within the vessels. The buildup is a gradual process in which the artery gradually becomes blocked, narrowed, or weakened. When this condition affects the arteries of the heart, it is called coronary heart disease (coronary artery disease). Of the peripheral arteries, those of the legs are most often affected. Other arteries frequently affected include those supplying blood to the kidneys or arms.[29]

As used herein, the term "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion or as described elsewhere throughout the specification.

As used herein, the term "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that stimulates promoter activity and may be an innate element of the promoter or a heterologous element inserted to enhance the level or tissue specificity of a promoter. It is capable of operating in both orientations (sense or antisense), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Any promoter known in the art which regulates the expression of the shRNA or RNA coding sequence is envisioned in the practice of the invention.

As used herein, the term "reporter element" or "marker" is meant a polynucleotide that encodes a polypeptide capable of being detected in a screening assay. Examples of polypeptides encoded by reporter elements include, but are not limited to, lacZ, GFP, luciferase, and chloramphenicol acetyltransferase. See, for example, U.S. Pat. No. 7,416,849. Many reporter elements and marker genes are known in the art and envisioned for use in the inventions disclosed herein.

As used herein, the term "RNA transcript" refers to the product resulting from RNA polymerase catalyzed transcription of a DNA sequence. "Messenger RNA transcript (mRNA)" refers to the RNA that is without introns and that can be translated into protein by the cell.

As used herein, the terms "small interfering" or "short interfering RNA" or "siRNA" refer to an RNA duplex of nucleotides that is targeted to a desired gene and is capable of inhibiting the expression of a gene with which it shares homology. The RNA duplex comprises two complementary single-stranded RNAs of 15, 16, 17, 18, 19, 20, 21, 22, 23, 24, or 25 nucleotides that form 15, 16, 17, 18, 19, 20, 21, 22, 23, 24, or 25 base pairs and possess 3' overhangs of two nucleotides. The RNA duplex is formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. The duplex can be 29, 28, 27, 26, 25, 24, 23, 22, 21, 20, 19, 18, 17, 16, 15, 14, 13, 12, 11 or 10 nucleotides in length. The length of the duplex can be 17-25 nucleotides in length. The duplex RNA can be expressed in a cell from a single construct.

As used herein, the term "shRNA" (small hairpin RNA) refers to an RNA duplex wherein a portion of the siRNA is part of a hairpin structure (shRNA). In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some aspects, the overhang is a 3' or a 5' overhang 0, 1, 2, 3, 4 or 5 nucleotides in length. In one aspect of this invention, a nucleotide sequence in the vector serves as a template for the expression of a small hairpin RNA, comprising a sense region, a loop region and an antisense region. Following expression the sense and antisense regions form a duplex. It is this duplex, forming the shRNA, which hybridizes to, for example, the PHD2 mRNA and reduces expression of PHD2, allowing accumulation of HIF-1α and inducing neo-angiogenesis.

As used herein, the term "treating" refers to ameliorating at least one symptom of, curing and/or preventing the development of a disease or disorder such as for example, but not limited to, ischemic heart disease, peripheral vascular disease, and decubitis ulcer.

As used herein, the term "vector" refers to any viral or non-viral vector, as well as any plasmid, cosmid, phage or binary vector in double or single stranded linear or circular form that may or may not be self transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this invention.

BRIEF DESCRIPTION OF THE DRAWINGS

Advantages of the present invention will be readily appreciated as the same becomes better understood by reference to the following detailed description when considered in connection with the accompanying drawings.

FIG. 1 discloses SEQ ID NOS 18-25, respectively, in order of appearance.

FIG. 9. Supplementary Table 1: The primer sets used in the RT-PCR amplification reaction. Six gene's relation to the angiogenesis in different pathway were tested after PHD2 gene knocking down. FIG. 9 discloses SEQ ID NOS 26-37, respectively, in order of appearance.

Figure 1:
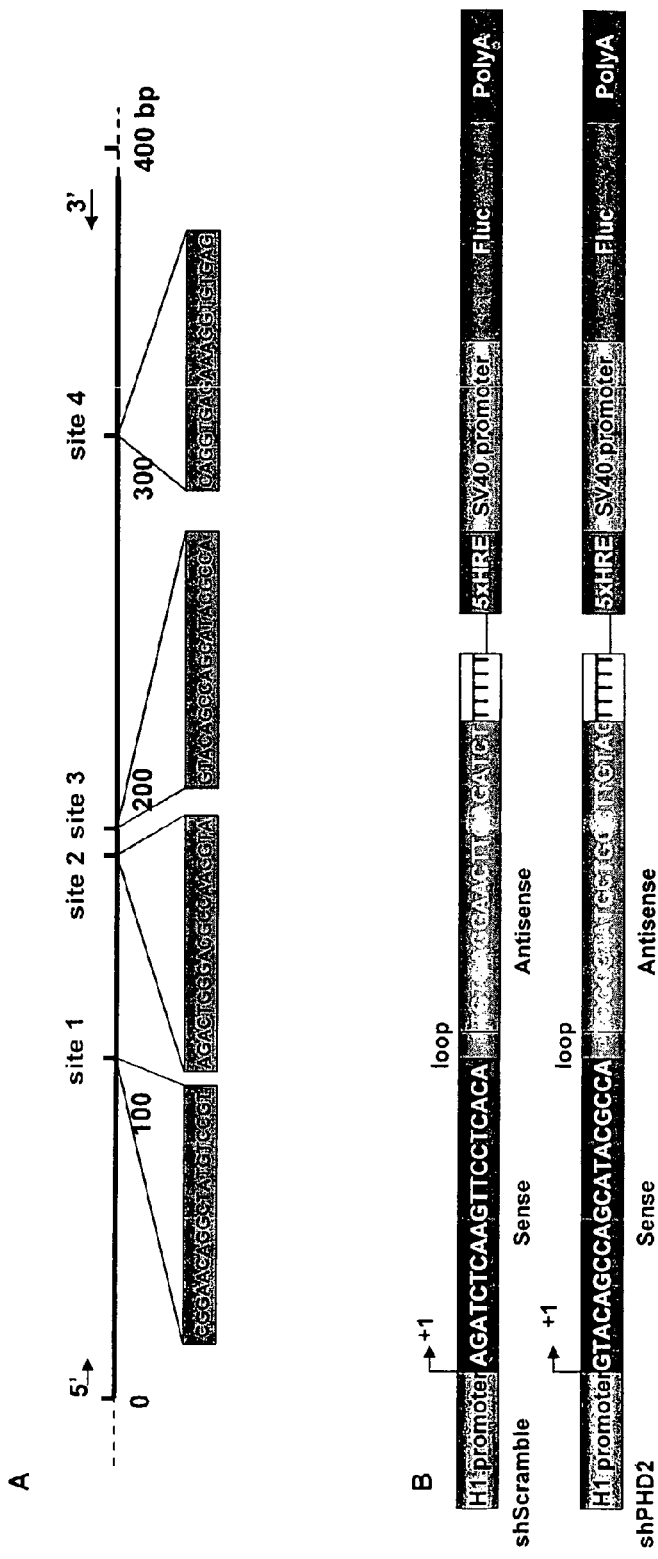
FIG. 1. Schema of the shPHD2 knockdown sites and reporter constructs. A, Individual sequences of 4 small interfering RNA target sites against the PHD2 gene. B, Schema of classic hairpin carrying the Site 2 sequence (shPHD2) and control hairpin carrying the scramble sequence (shScramble). The H1 promoter drives the expression of a hairpin structure in which the sense and antisense strands of the small interfering RNA are connected by a 9-bp long loop sequence. In addition, a separate 5XHRE-SV40 promoter driving Fluc is used to track shRNA activity in vitro and in vivo. 5XHRE, 5 repeat of hypoxia response elements; Sv40, simian virus 40.

In general, included in the invention is a vector comprising a polynucleotide sequence, and a promoter operably-linked to an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment. The second segment, located immediately 3' of the first segment, encodes a loop structure containing from 4-10 nucleotides (i.e., 4, 5, 6, 7, 8, 9, 10). The nucleic acid sequence is expressed as an siRNA and functions as a small hairpin RNA molecule (shRNA) targeted against a designated nucleic acid sequence.

More specifically, the present invention includes compositions and methods for selectively reducing the expression of the gene product from the HIF-1α PHD2 gene in a eukaryotic cell, as well as for treating diseases in mammals, such as for example, but not limited to, humans, mice and rats, caused by the expression of the gene. The present invention provides a vector comprising a polynucleotide sequence which comprises a nucleic acid sequence encoding a small interfering RNA molecule (siRNA) targeted against the HIF-1α PHD2. The siRNA forms a hairpin structure comprising a duplex structure and a loop structure. The loop structure may contain from 4 to 10 nucleotides, such as 4, 5 or 6 nucleotides. The duplex is less than 30 nucleotides in length, such as from 10 to 27 nucleotides. The siRNA may further comprise an overhang region. Such an overhang may be a 3' overhang region or a 5' overhang region. The overhang region may be, for example, 1, 2, 3, 4, 5, or 6 nucleotides in length.

In another aspect of the invention, the invention is directed to compositions and methods for selectively reducing the expression of the gene product from the ASPH gene in a eukaryotic cell, as well as for treating diseases in mammals, such as for example, but not limited to, humans, mice and rats, caused by the expression of the gene. The present invention provides a vector comprising a polynucleotide sequence which comprises a nucleic acid sequence encoding a small interfering RNA molecule (siRNA) targeted against the ASPH gene. The siRNA forms a hairpin structure comprising a duplex structure and a loop structure. The loop structure may contain from 4 to 10 nucleotides, such as 4, 5, 6, 7, 8, 9, 10 nucleotides. The duplex is less than 30 nucleotides in length, such as from 10 to 27 nucleotides. The siRNA may further comprise an overhang region. Such an overhang may be a 3' overhang region or a 5' overhang region. The overhang region may be, for example, 1, 2, 3, 4, 5, 6 nucleotides in length.

In another aspect of the invention, the invention is directed to compositions and methods for selectively reducing the expression of the gene product from the HIF-1α gene in a eukaryotic cell, as well as for treating diseases in mammals, such as for example, but not limited to, humans, mice and rats, caused by the expression of the gene. The present invention provides a vector comprising a polynucleotide sequence which comprises a nucleic acid sequence encoding a small interfering RNA molecule (siRNA) targeted against the HIF-1α gene. The siRNA forms a hairpin structure comprising a duplex structure and a loop structure. The loop structure may contain from 4 to 10 nucleotides, such as 4, 5, 6, 7, 8, 9, 10 nucleotides. The duplex is less than 30 nucleotides in length, such as from 10 to 27 nucleotides. The siRNA may further comprise an overhang region. Such an overhang may be a 3' overhang region or a 5' overhang region. The overhang region may be, for example, 1, 2, 3, 4, 5, 6 nucleotides in length.

The vector of the invention may further comprise a promoter. Examples of promoters include regulatable promoters and constitutive promoters. For example, the promoter may be a CMV or RSV promoter. The vector may further comprise a polyadenylation signal, such as a synthetic minimal polyadenylation signal. Many such promoters are known in the art and are envisioned for use in this invention. In other instances, the promoter may be a tissue specific promoter, such as a cardiac tissue specific promoter.

The vector may further comprise one or more marker genes or reporter genes. Many marker genes and reporter genes are known in the art. The present invention contemplates use of one or more marker genes and/or reporter genes known in the art in the practice of the invention. The marker genes or reporter genes provide a method to track expression of one or more linked genes. The marker genes or reporter genes upon expression within the cell, provide products, usually proteins, detectable by spectroscopic, photochemical, biochemical, immunochemical, chemical, or other physical means. Gene expression products, whether from the gene of interest, marker genes or reporter genes may also be detected by labeling. Labels envisioned for use in the inventions included herein include, but are not limited to, fluorescent dyes, electron-dense reagents, enzymes (for example, as commonly used in an ELISA), biotin, digoxigenin, or haptens and proteins which can be made detectable, e.g., by incorporating a radiolabel into the peptide or used to detect antibodies specifically reactive with the peptide. See, for example, U.S. Pat. No. 7,419,779.

The nucleotide sequence of PHD2 is known in the art and set forth herein. In one aspect of the invention, nucleic acid molecules targeted to additional RNA interference sites may be designed from the PHD2 sequence and used in the practice of this invention either alone, with each other in any combination, or in conjunction with the polynucleotides having SEQ ID NO:9 and/or SEQ ID NO: 10 alone or in any combination. By way of example, any nucleotide sequence of 15, 16, 17, 18, 19, 20, 21, 22, 23, 24, 25, 26, 27, 28, 29 or 30 consecutive nucleotides of the PHD2 gene is one aspect of this invention. Thus, HIF-1α PHD2 nucleotide nos. 1-19, 2-20, 3-21, 4-22 etc.; or 1-15 or 16 or 17 or 18 or 20; or 2-16 or 17 or 18 or 19 and so forth through to the end of the PHD2 gene are envisioned as RNA interference sites of this invention.

The nucleotide sequence of ASPH is known in the art. In one aspect of the invention, nucleic acid molecules targeted to additional RNA interference sites may be designed from the ASPH sequence and used in the practice of this invention either alone, with each other in any combination, or in conjunction with the polynucleotides having SEQ ID NO:14 and/or SEQ ID NO: 15 alone or in any combination. By way of example, any nucleotide sequence of 15, 16, 17, 18, 19, 20, 21, 22, 23, 24, 25, 26, 27, 28, 29 or 30 consecutive nucleotides of the ASPH gene is an aspect of this invention. Thus, ASPH nucleotide Nos. 1-19, 2-20, 3-21, 4-22 etc., or 1-15 or 16 or 17 or 18 or 20; 2-16 or 17 or 18 or 19 through to the end of the ASPH gene (the entire nucleotide sequence is presented in SEQ ID NO: 13) are envisioned as RNA interference sites of this invention.

The nucleotide sequence of HIF-1α is known in the art. In one aspect of the invention, nucleic acid molecules targeted to additional RNA interference sites may be designed from the HIF-1α sequence and used in the practice of this invention either alone, with each other in any combination, or in conjunction with the polynucleotides having SEQ ID NO: 16 alone or in any combination. By way of example, any nucleotide sequence of 15, 16, 17, 18, 19, 20, 21, 22, 23, 24, 25, 26, 27, 2,8 29 or 30 consecutive nucleotides of the HIF-1α gene is an aspect of this invention. Thus, HIF-1α nucleotide Nos. 1-18, 2-19, 3-20, 4-21 etc. or 1-15 or 16 or 17 or 19 or 20; 2-17 or 16 or 18 or 19 through to the end of the HIF-1α gene (GENBANK Accession No. NM_001530; the nucleotide sequence is presented in SEQ ID NO: 17) are envisioned as RNA interference sites of this invention.

The invention provides, inter alia, a method of treating a mammal by administering to the mammal a composition comprising the vectors described herein. In one aspect of the invention, multiple vectors each encoding a different shRNA (targeted to a different designated nucleic acid sequence) may be administered simultaneously or consecutively to the mammal. An individual vector may encode shRNAs targeted to different areas of the same gene; i.e., comprising a shRNA having SEQ ID NO: 9 and shRNA having SEQ ID NO: 10. In another aspect, an individual vector may encode multiple copies of shRNA comprising SEQ ID NO: 9 or multiple copies of shRNA comprising SEQ ID NO: 10. In another aspect, an individual vector may encode multiple shRNAs, the vector comprising shRNA comprising SEQ ID NO: 9 or shRNA comprising SEQ ID NO: 10 in any ratio. Similarly, an individual vector may encode multiple shRNAs, the vector comprising shRNA comprising SEQ ID NO: 14 or shRNA comprising SEQ ID NO: 15 alone or in any combination. Likewise, an individual vector may encode shRNA comprising SEQ ID NO: 16. An individual vector may encode shRNA comprising one or more of SEQ ID NO: 9, 10, 14, 15, 16 and any combination thereof.

Any combination of the vectors described herein may be administered simultaneously or consecutively. For example, vectors encoding shRNA targeted to HIF-1α PHD2, ASPH and HIF-1α are disclosed herein. Any combination of the vectors described herein are used in the treatment of diseases or disorders in mammals. In addition, an individual vector may comprise multiple polynucleotides each of which encodes an shRNA which targets a gene selected from the group consisting of HIF-1α PHD2, ASPH and HIF-1α.

If there is sufficient identity among a family of homologous genes within an organism, a duplex region can be designed that would down regulate a plurality of genes simultaneously. See, for example, U.S. Pat. No. 7,410,944. For example, due to the conserved nature of the PHD2 gene family, the ASPH gene family and the HIF-1α family, the sequence of the duplex region can be chosen with the aid of sequence comparison to target only the desired gene sequence. Thus, designing a duplex region which would simultaneously knock down one or more members of the PHD2 gene family (ie, SEQ ID NOs: 2, 4, 6, 8) or a member of the ASPH family (see, reference 30) or a member of the HIF-1α family is another aspect of the invention.

In another aspect of the invention, tissues or cells can be transfected with two or more vectors, at least one vector containing the nucleic acid(s) encoding the siRNA(s), the other vector containing a nucleotide sequence encoding a marker gene and/or a reporter gene. As a nonlimiting example, tissues or cells can be transfected one or more times with multiple vectors, for example, one vector encoding a PHD2 shRNA, another encoding a ASPH shRNA and another encoding a HIF-1α shRNA. The reporter gene or marker gene may be on the same vector as the shRNA or a different vector. The selection of a suitable promoter, enhancer, selection gene and/or signal sequence is deemed to be within the scope of one of ordinary skill in the art without undue experimentation.

siRNA

According to the invention, an siRNA or RNA duplex corresponding to a region of a target gene to be down-regulated or knocked-down is expressed in the cell. The RNA duplex is substantially identical (typically at least about 80% identical, and more typically at least about 90% identical) in sequence to the sequence of the gene targeted for down regulation. siRNA duplexes are described and well known in the art. See, for example, U.S. Pat. No. 7,410,944.

In one embodiment, the shRNA is a "hairpin" or stem-loop RNA molecule, comprising a sense region, a loop region and an antisense region complementary to the sense region. In other embodiments the shRNA comprises two distinct RNA molecules that are non-covalently associated to form a duplex. See, for example, U.S. Pat. No. 7,195,916.

When appropriately targeted via its nucleotide sequence to a specific mRNA in cells, an siRNA can specifically suppress gene expression through a process known as RNA interference (RNAi). siRNAs can reduce the cellular level of specific mRNAs, and decrease the level of proteins coded by such mRNAs. siRNAs utilize sequence complementarity to target an mRNA for destruction, and are sequence-specific. Thus, they can be highly target-specific, and in mammals have been shown to target mRNAs encoded by different alleles of the same gene.

It should further be noted that full complementarity between the target sequence and the antisense siRNA is not required. That is, the resultant antisense siRNA is sufficiently complementary with the target sequence. The sense strand is substantially complementary with the antisense strand to anneal (hybridize) to the antisense strand under biological conditions.

Hybridization

In particular, the complementary polynucleotide sequence of shRNA can be designed to specifically hybridize to a particular region of a desired target protein or mRNA to interfere with replication, transcription, or translation. The term "hybridize" or variations thereof, refers to a sufficient degree of complementarity or pairing between an antisense nucleotide sequence and a target DNA or mRNA such that stable and specific binding occurs there between. In particular, 100% complementarity or pairing is desirable but not required. Specific hybridization occurs when sufficient hybridization occurs between the antisense nucleotide sequence and its intended target nucleic acids in the substantial absence of non-specific binding of the antisense nucleotide sequence to non-target sequences under predetermined conditions, e.g., for purposes of in vivo treatment, preferably under physiological conditions. Preferably, specific hybridization results in the interference with normal expression of the gene product encoded by the target DNA or mRNA.

For example, an antisense nucleotide sequence can be designed to specifically hybridize to the replication or transcription regulatory regions of a target gene, or the translation regulatory regions such as translation initiation region and exon/intron junctions, or the coding regions of a target mRNA.

siRNA: Synthesis

As is generally known in the art, commonly used oligonucleotides are oligomers or polymers of ribonucleic acid or deoxyribonucleic acid having a combination of naturally-occurring purine and pyrimidine bases, sugars and covalent linkages between nucleosides including a phosphate group in a phosphodiester linkage. However, it is noted that the term "oligonucleotides" also encompasses various non-naturally occurring mimetics and derivatives, i.e., modified forms, of naturally-occurring oligonucleotides as described below.

siRNA molecules of the invention can be prepared by any method known in the art for the synthesis of DNA and RNA molecules. These include techniques for chemically synthesizing oligodeoxy-ribonucleotides and oligo-ribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

siRNA molecules can be chemically synthesized using appropriately protected ribonucleoside phosphoramidites and a conventional DNA/RNA synthesizer. Custom siRNA synthesis services are available from commercial vendors such as Ambion (Austin, Tex., USA) and Dharmacon Research (Lafayette, Colo., USA). See, for example, U.S. Pat. No. 7,410,944.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone. An antisense nucleic acid of the invention can be constructed using chemical synthesis or enzymatic ligation reactions using procedures known in the art. An antisense oligonucleotide can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

The siRNA molecules of the invention can be various modified equivalents of the structures of any HIF-1α PHD2 siRNA, any ASPHD siRNA, any HIF-1α siRNA. A "modified equivalent" means a modified form of a particular siRNA molecule having the same target-specificity (i.e., recognizing the same mRNA molecules that complement the unmodified particular siRNA molecule). Thus, a modified equivalent of an unmodified siRNA molecule can have modified ribonucleotides, that is, ribonucleotides that contain a modification in the chemical structure of an unmodified nucleotide base, sugar and/or phosphate (or phosphodiester linkage). See, for example, U.S. Pat. No. 7,410,944.

Preferably, modified siRNA molecules contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like. See, for example, U.S. Pat. No. 7,410,944.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See, for example, U.S. Pat. No. 7,410,944.

Examples of the non-phosphorous containing backbones described above are known in the art, e.g., U.S. Pat. No. 5,677,439, each of which is herein incorporated by reference. See, for example, U.S. Pat. No. 7,410,944.

Modified forms of siRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxy methyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyl uridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyl adenosine, beta-D-mannosylqueosine, uridine-5-oxyacetic acid, 2-thiocytidine, threonine derivatives, and the like. See, for example, U.S. Pat. No. 7,410,944.

In addition, modified siRNA compounds can also have substituted or modified sugar moieties, e.g., 2'-O-methoxyethyl sugar moieties. See, for example, U.S. Pat. No. 7,410, 944.

Preferably, the 3' overhangs of the siRNAs of the present invention are modified to provide resistance to cellular nucleases. In one embodiment the 3' overhangs comprise 2'-deoxyribonucleotides.

Additional siRNA compounds targeted at different sites of the mRNA corresponding to HIF-1 α PHD2 can also be designed and synthesized according to general guidelines provided herein and generally known to skilled artisans. In one aspect, shRNa targeted to sites 2 and 3 of the HIF-1 α PHD2 gene are disclosed herein. Additional siRNA compounds targeted at different sites of the mRNA corresponding to ASPH and at different sites of the mRNA corresponding to HIF-1 HIF-1α can also be designed and synthesized according to general guidelines provided herein and generally known to skilled artisans.

Additionally, to assist in the design of siRNAs for the efficient RNAi-mediated silencing of any target gene, several siRNA supply companies maintain web-based design tools that utilize these general guidelines for "picking" siRNAs when presented with the mRNA or coding DNA sequence of the target gene. Examples of such tools can be found at the web sites of Dharmacon, Inc. (Lafayette, Colo.), Ambion, Inc. (Austin, Tex.). As an example, picking siRNAs involves choosing a site/sequence unique to the target gene (i.e., sequences that share no significant homology with genes other than the one being targeted), so that other genes are not inadvertently targeted by the same siRNA designed for this particular target sequence.

Another criterion to be considered is whether or not the target sequence includes a known polymorphic site. If so, siRNAs designed to target one particular allele may not effectively target another allele, since single base mismatches between the target sequence and its complementary strand in a given siRNA can greatly reduce the effectiveness of RNAi induced by that siRNA. Given that target sequence and such design tools and design criteria, an ordinarily skilled artisan apprised of the present disclosure should be able to design and synthesized additional siRNA compounds useful in reducing the mRNA level of HIF-1α PHD2, ASPH and HIF-1 HIF-1 α.

siRNA: Administration

The present invention provides a composition of a polymer or excipient and one or more vectors encoding one or more shRNA molecules. The vector can be formulated into a pharmaceutical composition with suitable carriers and administered into a mammal using any suitable route of administration.

Because of this precision, side effects typically associated with traditional drugs can be reduced or eliminated. In addition, siRNA are relatively stable, and like antisense, they can also be modified to achieve improved pharmaceutical characteristics, such as increased stability, deliverability, and ease of manufacture. Moreover, because siRNA molecules take advantage of a natural cellular pathway, i.e., RNA interference, they are highly efficient in destroying targeted mRNA molecules. As a result, it is relatively easy to achieve a therapeutically effective concentration of an siRNA compound in a subject. See, for example, U.S. Pat. No. 7,410,944.

siRNA compounds may be administered to mammals by various methods through different routes. They can also be delivered directly to a particular organ or tissue by any suitable localized administration methods such as direct injection into a target tissue. Alternatively, they may be delivered encapsulated in liposomes, by iontophoresis, or by incorporation into other vehicles such as hydrogels, cyclodextrins, biodegradable nanocapsules, and bioadhesive microspheres.

In vivo inhibition of specific gene expression by RNAi injected intravenously has been achieved in various organisms including mammals. See, for example, Song et al.[31] One route of administration of shRNA molecules of the invention includes direct injection of the vector at a desired tissue site, such as for example, into diseased or non-diseased cardiac tissue, into ischemic heart tissue, into tissue suffering from peripheral vascular disease and decubitus ulcers.

In one aspect of the invention, one or more vectors comprising one or more of shRNA of the invention can be readministered an unlimited number of times after a first administration at any time interval or intervals after the first administration.

siRNA: Pharmaceutical Compositions

The shRNA encoding nucleic acids of the present invention can be formulated in pharmaceutical compositions, which are prepared according to conventional pharmaceutical compounding techniques. See, e.g., *Remington's Pharmaceutical Sciences*, 18th Ed. (1990, Mack Publishing Co., Easton, Pa.). The pharmaceutical compositions of the invention comprise a therapeutically effective amount of the vector encoding shRNA. These compositions can comprise, in addition to the vector, a pharmaceutically acceptable excipient, carrier, buffer, stabilizer or other materials well known in the art. Such materials should be non-toxic and should not interfere with the efficacy of the active ingredient. The carrier can take a wide variety of forms depending on the form of preparation desired for administration, e.g., intravenous, oral, intramuscular, subcutaneous, intrathecal, epineural or parenteral.

When the vectors of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation In another aspect of the invention, the vectors of the invention can be suitably formulated and introduced into the environment of the cell by any means that allows for a sufficient portion of the sample to enter the cell to induce gene silencing, if it is to occur. Many formulations for vectors are known in the art and can be used so long as the vectors gain entry to the target cells so that it can act.

For example, the vectors can be formulated in buffer solutions such as phosphate buffered saline solutions comprising liposomes, micellar structures, and capsids. The pharmaceutical formulations of the vectors of the invention can also take the form of an aqueous or anhydrous solution or dispersion, or alternatively the form of an emulsion or suspension. The pharmaceutical formulations of the vectors of the present invention may include, as optional ingredients, solubilizing or emulsifying agents, and salts of the type that are well-known in the art. Specific non-limiting examples of the carriers and/or diluents that are useful in the pharmaceutical formulations of the present invention include water and physiologically acceptable saline solutions. Other pharmaceutically acceptable carriers for preparing a composition for administration to an individual include, for example, solvents or vehicles such as glycols, glycerol, or injectable organic esters. A pharmaceutically acceptable carrier can contain physiologically acceptable compounds that act, for example, to stabilize or to increase the absorption of the shRNA encoding vector. Other physiologically acceptable carriers include, for example, carbohydrates, such as glucose, sucrose or dextrans, antioxidants, such as ascorbic acid or glutathione, chelating agents, low molecular weight proteins or other stabilizers or excipients, saline, dextrose solutions, fructose solutions, ethanol, or oils of animal, vegetative or synthetic origin. The carrier can also contain other ingredients, for example, preservatives.

It will be recognized that the choice of a pharmaceutically acceptable carrier, including a physiologically acceptable compound, depends, for example, on the route of administration of the composition. The composition containing the vectors can also contain a second reagent such as a diagnostic reagent, nutritional substance, toxin, or additional therapeutic agent. Many agents useful in the treatment of cardiac disease are known in the art and are envisioned for use in conjunction with the vectors of this invention.

Formulations of vectors with cationic lipids can be used to facilitate transfection of the vectors into cells. For example, cationic lipids, such as lipofectin, cationic glycerol derivatives, and polycationic molecules, such as polylysine, can be used. Suitable lipids include, for example, Oligofectamine and Lipofectamine (Life Technologies) which can be used according to the manufacturer's instructions.

Suitable amounts of vector must be introduced and these amounts can be empirically determined using standard methods. Typically, effective concentrations of individual vector species in the environment of a cell will be about 50 nanomolar or less 10 nanomolar or less, or compositions in which concentrations of about 1 nanomolar or less can be used. In other aspects, the methods utilize a concentration of about 200 picomolar or less and even a concentration of about 50 picomolar or less can be used in many circumstances. One of skill in the art can determine the effective concentration for any particular mammalian subject using standard methods.

The siRNA is preferably administered in a therapeutically effective amount. The actual amount administered, and the rate and time-course of administration, will depend on the nature and severity of the condition, disease or disorder being treated. Prescription of treatment, for example, decisions on dosage, timing, etc., is within the responsibility of general practitioners or specialists, and typically takes account of the disorder, condition or disease to be treated, the condition of the individual mammalian subject, the site of delivery, the method of administration and other factors known to practitioners. Examples of techniques and protocols can be found in Remington's Pharmaceutical Sciences 18th Ed. (1990, Mack Publishing Co., Easton, Pa.).

Alternatively, targeting therapies can be used to deliver the shRNA encoding vectors more specifically to certain types of cell, by the use of targeting systems such as antibodies or cell specific ligands. Targeting can be desirable for a variety of reasons, e.g., if the agent is unacceptably toxic, or if it would otherwise require too high a dosage, or if it would not otherwise be able to enter the target cells.

siRNA: Gene Therapy siRNA can also be delivered into mammalian cells, particularly human cells, by a gene therapy approach, using a DNA vector from which siRNA compounds in, e.g., small hairpin form (shRNA), can be transcribed directly. Recent studies have demonstrated that while double-stranded siRNAs are very effective at mediating RNAi, short, single-stranded, hairpin-shaped RNAs can also mediate RNAi, presumably because they fold into intramolecular duplexes that are processed into double-stranded siRNAs by cellular enzymes. This discovery has significant and far-reaching implications, since the production of such shRNAs can be readily achieved in vivo by transfecting cells or tissues with DNA vectors bearing short inverted repeats separated by a small number of (e.g., 3, 4, 5, 6, 7, 8, 9) nucleotides that direct the transcription of such small hairpin RNAs. Additionally, if mechanisms are included to direct the integration of the vector or a vector segment into the host-cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice.

Gene therapy is carried out according to generally accepted methods as are known in the art. See, for example, U.S. Pat. Nos. 5,837,492 and 5,800,998 and references cited therein. Vectors in the context of gene therapy are meant to include those polynucleotide sequences containing sequences sufficient to express a polynucleotide encoded therein. If the polynucleotide encodes an shRNA, expression will produce the antisense polynucleotide sequence. Thus, in this context, expression does not require that a protein product be synthesized. In addition to the shRNA encoded in the vector, the vector also contains a promoter functional in eukaryotic cells. The shRNA sequence is under control of this promoter. Suitable eukaryotic promoters include those described elsewhere herein and as are known in the art. The expression vector may also include sequences, such as selectable markers, reporter genes and other regulatory sequences conventionally used.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the nucleic acid sequence encoding a siRNA sequence that are in the cell.

Methods

RNA Interference of Mouse Prolyl 4-Hydroxylase-2 Gene in Culture Cell

Mouse PHD2 gene was cloned from mouse embryonic stem cell after comparing human and rat homolog genes. Four sequences of RNA interference sites were designed. The targeting sequences are shown in FIG. 1A. Sequence for the short hairpin scramble (shScramble) antisense is 5'-TGT- GAGGAACTTGAGATCT-3' (control) (SEQ ID No: 11). Construction of the H1 promoter driving sense and antisense, respectively, was performed as described.[9] The fragment No 2 knocking down site was inserted after H1 promoter in the vector pSuper as described in the Oligoengine manual.

Cell Culture, Short Hairpin RNA Transfection, and Hypoxia Exposure.

Mouse C2C12 myoblasts were cultured in DMEM medium (high glucose) supplemented with 10% fetal bovine serum as described in the ATCC protocol. The sense and antisense fragments of mouse PHD2 driven by the H1 promoter were cotransfected into C2C12 with the plasmid pCMV-firefly luciferase (Fluc) as control for equal transfection efficiency. Lipofectamine 2000 (Invitrogen) was used for the transfection according to manufacturer's protocol. Cells were cultured for 1 day after shRNA fragment transfection before being subjected to hypoxia. Hypoxia was achieved by placing cells in a hypoxia chamber filled with 5% $CO_2$, 1% $O_2$, and 94% $N_2$ at 37° C. Cells were then kept under hypoxic conditions for 48 hours. At the end of the hypoxic treatment, cells were harvested immediately to extract RNA and protein. Reverse transcriptase-polymerase chain reaction and Western blot analysis of angiogenic genes are as described herein.

Animal Surgery to Induce Myocardial Infarction.

Ligation of the mid left anterior descending artery was performed in adult female FVB mice (Charles River Laboratories, Wilmington, Mass.) by a single experienced surgeon. Myocardial infarction was confirmed by myocardial blanching and electrocardiographic changes. After waiting for 10 minutes, animals were then injected intramyocardially with 25 µg of shRNA plasmid at the peri-infarct zone (n=20) or 25 µg of shScramble plasmid (n=20) as control. In both groups, the volume of injection was 50 µL, using a 31-gauge Hamilton syringe. Study protocols were approved by the Stanford Animal Research Committee.

Optical Bioluminescence Imaging of Plasmid Gene Expression.

Cardiac bioluminescence imaging was performed with the Xenogen In Vivo Imaging System (Alameda, Calif.). After intraperitoneal injection of the reporter probe D-luciferin (150 mg/kg body weight), animals were imaged for 1 to 10 minutes. The same mice were scanned repetitively for a 4-week period according to the specific study design. Bioluminescence signals were quantified in maximum photons per second per centimeter squared per steradian (p/s/$cm_2$/sr) as described.[10] Briefly, after anesthetic induction with 2% isoflurane, reporter probe D-luciferin (Promega) was injected into the peritoneal cavity. The animals were immediately placed in a light-tight chamber and baseline gray-scale body-surface images were taken. Afterward, photons emitted from Fluc-luciferin photochemical reaction within the animal were acquired repetitively (1- to 10-minute acquisition time per image, 5 to 15 images per animal) until peak value was confirmed. We then averaged the 3 images with the highest p/s/$cm^2$/sr values and used that to represent the Fluc transgene expression for that mouse on that particular day.

Validation of In Vivo Bioluminescence Imaging with Ex Vivo Enzyme Assays.

A subset of the animals (n=5) were injected with varying doses of the shPHD2 plasmid (5, 10, 15, 20, and 25 µg). Animals were euthanized immediately after bioluminescence imaging. Different organs (heart, lungs, liver, kidney, and spleen) were excised and placed in 6-well plastic dishes containing D-luciferin (100 µmol/L). Ex vivo bioluminescence counts were determined. Afterward, these organs were homogenized and luciferase enzyme assays performed using a luminometer (Turner Design-20/20) as previously described.[11]

Analysis of Left Ventricular Function With Echocardiogram.

Echocardiography was performed before (Day −7) and after (Week 2, Week 4, Week 8) the left anterior descending artery ligation. The Siemens-Acuson Sequioa C512 system equipped with a multifrequency (8 to 14 MHZ) 15L8 transducer was used by an investigator blinded to group designation. Left ventricular end diastolic diameter and end systolic diameter were measured and used to calculate left ventricular fractional shortening by the formula: LVFS=[EDD−ESD]/EDD, in which LVFS is left ventricular fractional shortening, EDD is end diastolic diameter, and ESD is end systolic diameter.

Histological Examination.

Explanted hearts from study and control groups were embedded into OCT compound (Miles Scientific, Elkhart, Ind.). Frozen sections (5 µm thick) were processed for immunostaining. To detect microvascular density in the peri-infarct area, a rat anti-CD31 (BD Pharmingen) was used. The number of capillary vessels was counted by a blinded investigator in 10 randomly selected areas using a light microscope (×200 magnification). Additional samples were used to examine the infarction size by Masson's trichrome staining.

Statistical Analysis.

Analysis of variance and repeated-measures analysis of variance with post hoc testing as well as the 2-tailed Student t test were used. Differences were considered significant at probability values of <0.05. Unless specified, data are expressed as mean±SD.

3. Results

Mouse Prolyl Hydroxylase-2 Gene Isolation and Knocking Down in Culture Cells.

Figure 6:
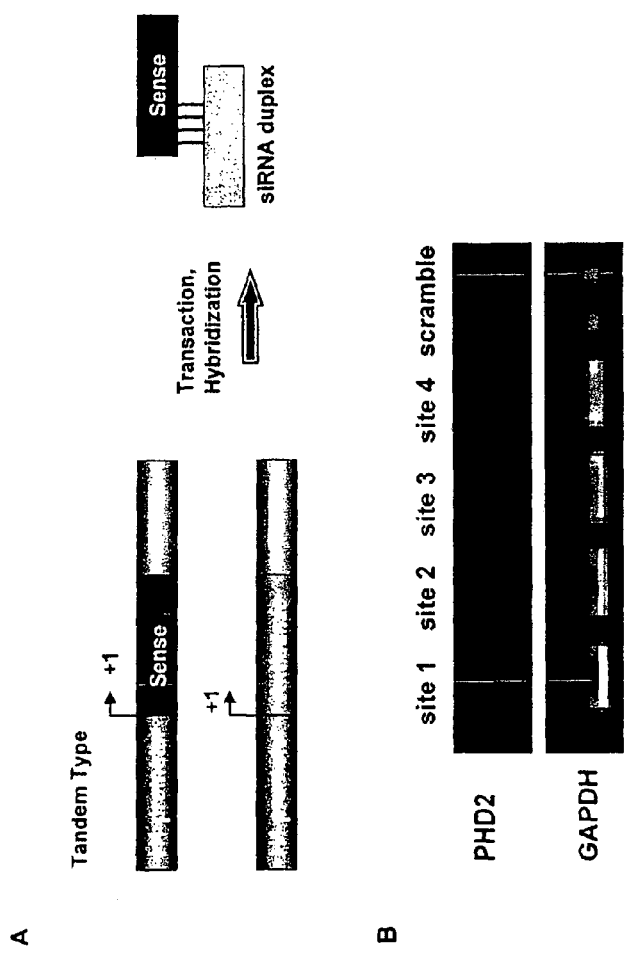
FIG. 6. Optimization of knocking-down target of mouse PHD2 gene. A, Schema of the tandem type shRNA structure. Two H1 promoters are used to drive the separate transcription of the sense and antisense strands. The two strands would then anneal to form a double-stranded siRNA complex within the cell. B, Forty-eight hours after siRNA fragment transfection, comparison of knocking-down efficiency was tested by RT-PCR of mouse PHD2 gene. Data shown here indicate that the site-2 siRNA fragment had the best interference efficiency.
Figure 7:
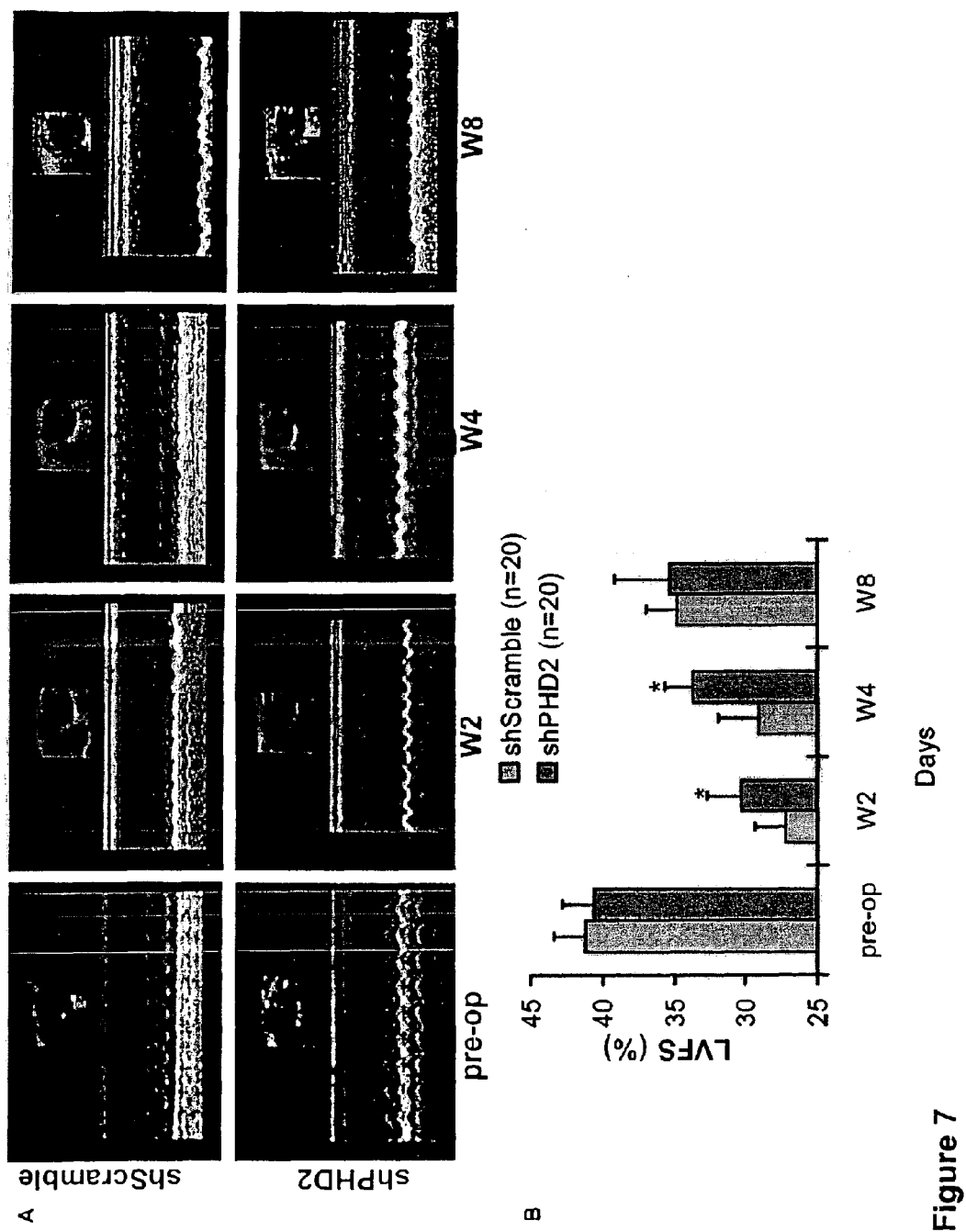
FIG. 7. Evaluation of cardiac function in infarcted mice following shRNA therapy. A, Representative echocardiogram (M-mode) of mice with LAD ligation following injection of shScramble plasmid (upper panel) versus shPHD2 plasmid (lower panel) at pre-surgery, week 2, week 4 and week 8. B, Quantitative analysis of left ventricular fractional shortening (LVFS) between the two groups. Animals injected with shPHD2 had significant improvement in LVFS at week 4 but not at week 8.

Based on the reported nucleotide sequence of PHD2 gene in rats and humans (www.genebank), we isolated the PHD2 DNA clone from mouse embryonic stem cell (Sv129 line). We designed 4 small interfering RNA sites (FIG. 1A) using commercially available web-based software (www.ambion). To determine the site that possesses the optimal knocking-down efficiency, we cloned the sense and antisense downstream of the H1 promoter, respectively, by polymerase chain reaction (FIG. 6). These 4 shRNA constructs were used to transfect C2C12 myoblasts in 6-well plates along with pCMV-luciferase plasmid used to confirm for equal transfection efficiency (data not shown). After 48 hours of cell culture, mRNA levels of PHD2 within C2C12 cells were measured by reverse transcriptase-polymerase chain reaction. Using the densitometric analysis software, Site 2 and Site 3 inhibition could degrade 50% to 60% of the mouse PHD2 mRNA, which were significantly better than Site 1 (15% to 25%) and Site 4 (20% to 30%) (FIG. 7).

In Vitro Characterization of Short Hairpin Prolyl Hydroxylase-2 Under Normoxia and Hypoxia Conditions.

Figure 2:
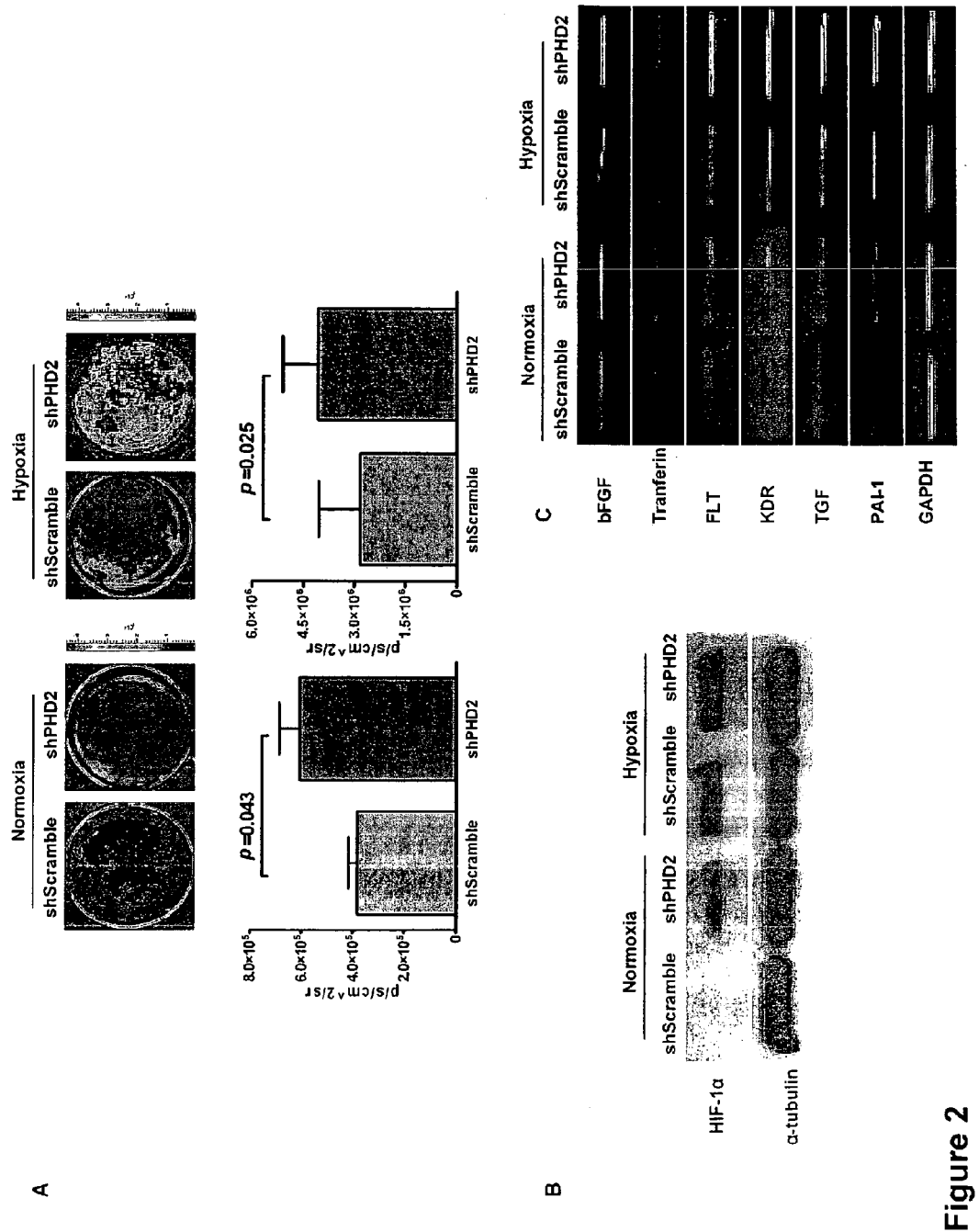
FIG. 2. In vitro characterization of mouse shPHD2. A, In vitro imaging results indicate that Fluc signals increased significantly in response to shPHD2 therapy during both normoxia and hypoxia conditions by binding of HIF-1α protein on the 5xHRE binding site. B, Western blot data show that levels of HIF-1α protein were more robust after shPHD2 plasmid transfection during normoxia and 6-hour hypoxia incubation. C, Reverse transcriptase-polymerase chain reaction analysis confirmed significant upregulation among 6 common genes involved in angiogenesis due to activation of the HIF-1α protein from knocking down PHD2 gene. GAPDH was used as the loading control.

To achieve in vivo inhibition by nonviral transfection, we constructed plasmid targeting PHD2 (shPHD2) by inserting the short hairpin structure downstream of the H1 promoter in a pSuper vector. A hypoxia sensing SXhypoxia response element (HRE)-SV40 promoter driving Fluc cassette was also inserted into the backbone of pSuper vector. The 5 copies of HRE derived from the erythropoietin gene are activated through binding of the HIF-1 complex[12] and thus allow us to monitor the efficacy of the upstream shPHD2 knockdown compared with the upstream shScramble control (FIG. 1B). In the normoxic condition, cells transfected with shPHD2 had significantly higher Fluc bioluminescence signals compared with cells transfected with shScramble control, indicating increased binding of 5XHRE-SV40 promoter by HIF-1α after shPHD2 knockdown (FIG. 2A). As expected, a similar but more robust trend was observed when the cells were exposed to the hypoxic condition. To confirm the imaging signals, nuclear extracts were isolated and Western blot analysis performed for detection of HIF-1α protein. As shown in FIG. 2B, robust HIF-1α stabilization was observed after exposure to hypoxia in shPHD2 transfected cells. The protein level was increased up to 50% after shPHD2 transfection. Upregulation of the HIF-1α pathway has been shown to activate several downstream genes responsible for stimulation of angiogenesis.[13] To examine if upregulation of HIF-1α by shRNA knockdown of PHD2 can exert similar effects, total RNAs were extracted from C2C12 cells transfected with shPHD2. As shown in FIG. 2C, 6 common genes related to angiogenesis were increased by approximately 30% after shPHD2 treatment. Thus, both physiological hypoxia and PHD2 knockdown can effectively stabilize HIF-1α and induce HIF-1α-dependent gene activation in cell cultures.

Correlation of Imaging Signals with Cell Numbers, Enzyme Assays, and Reverse Transcriptase-Polymerase Chain Reaction.

Figure 3:
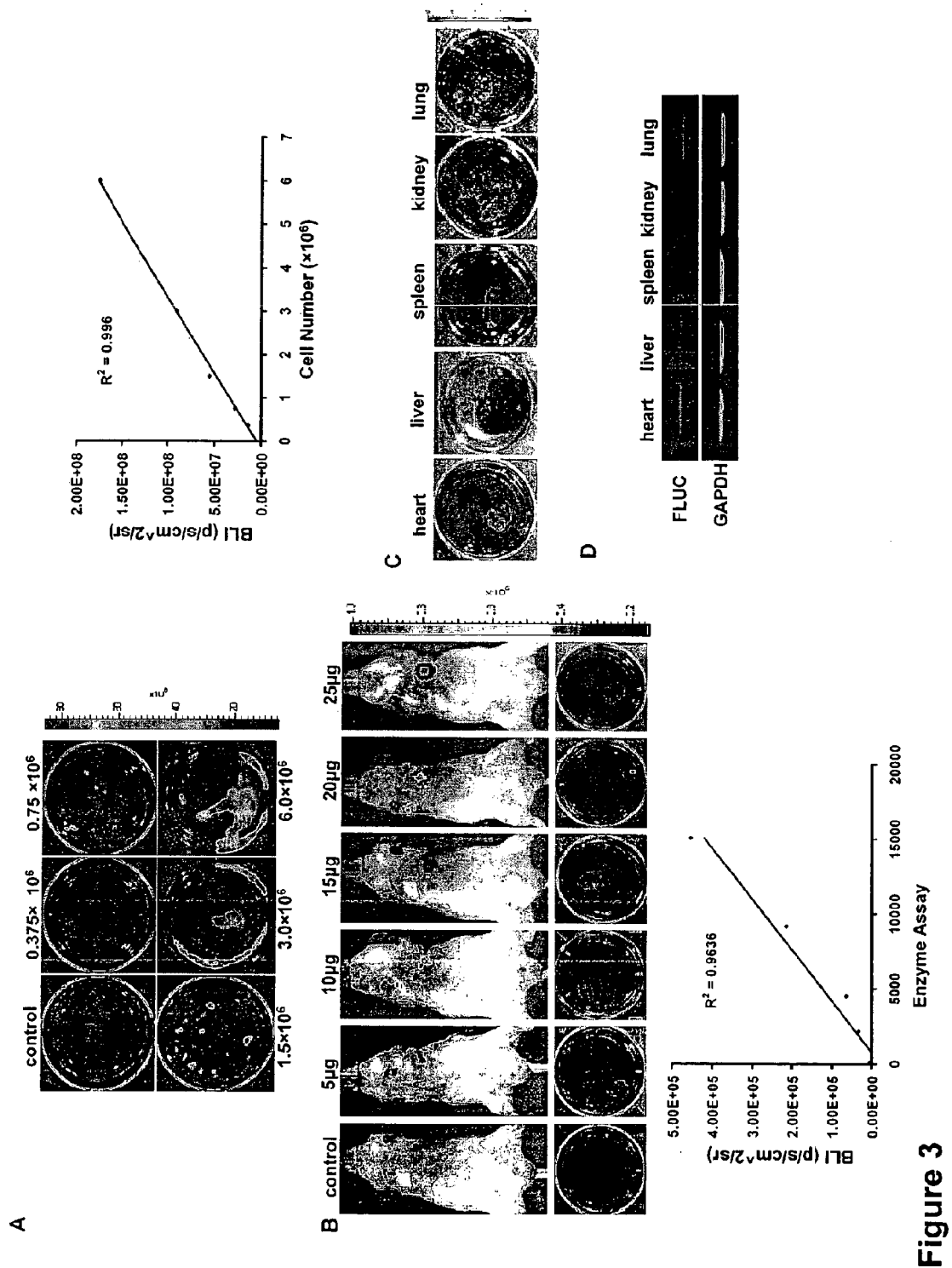
FIG. 3. Validation of imaging studies with traditional assays. A, Mouse C2C12 myoblasts were transfected with the shPHD2 or shScramble plasmid. A robust correlation exists between transfected cell numbers and bioluminescence signals ($r^2$=0.99). B, Mice were injected intramyocardially with different doses of shPHD plasmid (5 to 25 µg). Imaging analysis and enzyme assays of homogenized hearts show a robust correlation ($r^2$=0.96). C, Representative image showing bioluminescence signals emitted from different organs of animals injected with shPHD2 plasmid immediately after harvest. Reverse transcriptase-polymerase chain reaction confirmed the Fluc transgene expression in the heart, liver, and lung but not the spleen and kidney.

To determine the validity of in vivo bioluminescence imaging with more conventional ex vivo assays, we first transfected different numbers of mouse C2C12 myoblasts ($0.375 \times 10^6$ to $6 \times 10^6$) with 4 μg of shRNA plasmid in 6-well plates. As shown in FIG. 3A, the bioluminescence signals correlated robustly with in vitro Fluc enzyme activity ($r^2=0.99$) expressed as relative light unit per microgram protein. Next, a subset of the animals (n=5) were injected with different doses of the shPHD2 plasmid (5 to 25 μg). At 1 week, bioluminescence signals were detectable in the heart, which also correlated robustly with the ex vivo Fluc enzyme activity ($r^2=0.96$). Finally, to determine the plasmid biodistribution after intramyocardial delivery, we explanted different organs from these animals. With this experimental setup, both bioluminescence imaging and reverse transcriptase-polymerase chain reaction analysis demonstrate that presence of Fluc transgene expression in the heart, liver, and lung but not spleen and kidney (FIG. 3C).

Tracking Short Hairpin Prolyl Hydroxylase-2 Vector Using Bioluminescence Imaging in Living Animals.

Figure 4:
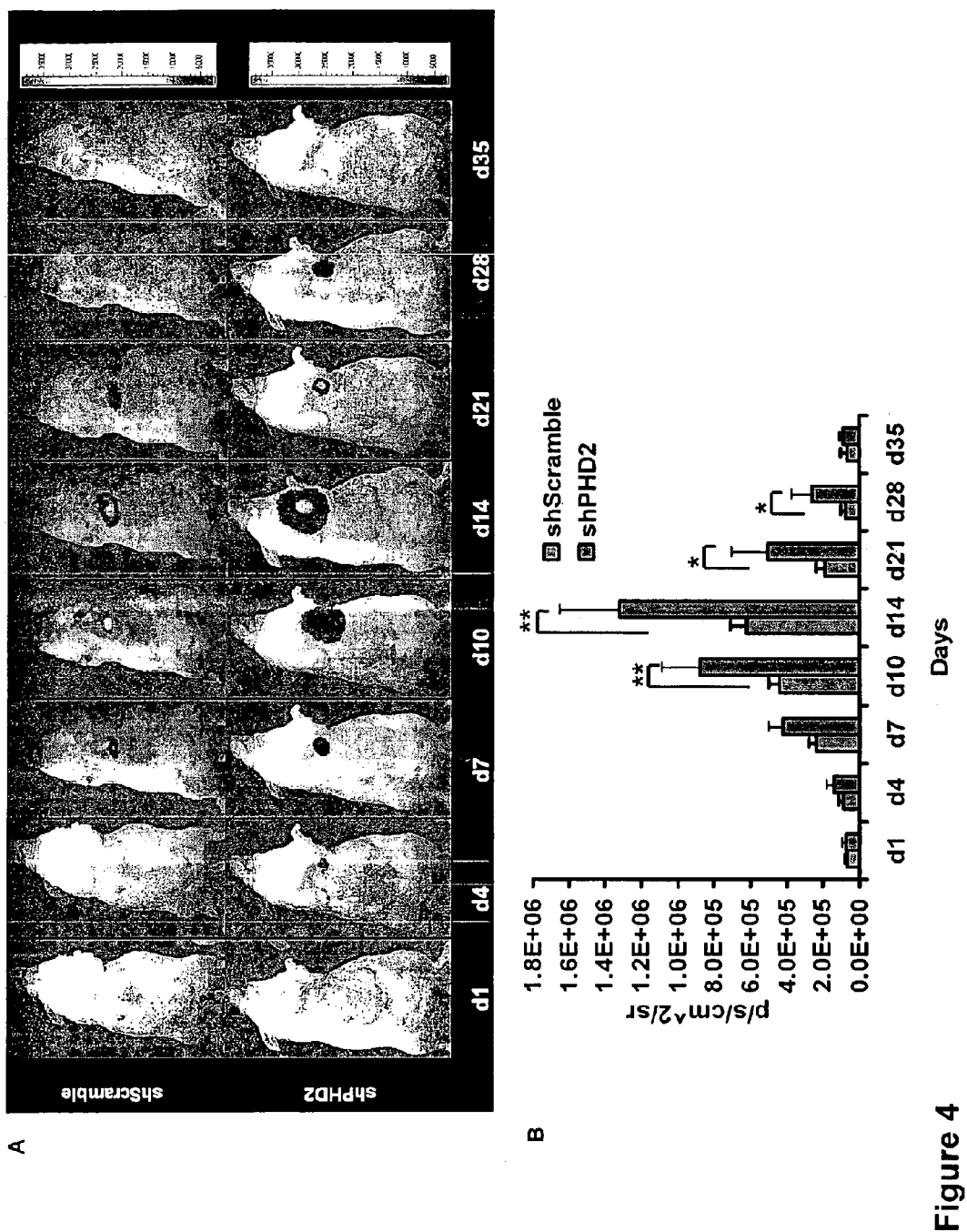
FIG. 4. Molecular imaging of shRNA plasmid fate after intramyocardial delivery. A, After myocardial infarction, activation of HIF-1α protein binds to the 5xHRE site to activate Fluc expression. Infarcted mice injected with shPHD2 (bottom row) had more robust Fluc signals compared with infarcted mice injected with shScramble (top row) due to knocking down of PHD2, which results in more HIF-1α protein binding to 5XHRE site. Peak transgene expression occurred within Weeks 1 to 2 as reflected by the Fluc imaging signals. B, Detailed quantitative analysis of Fluc bioluminescence signals from all animals injected with shPHD2 or shScramble plasmid with left anterior descending artery ligation. Signal activity is expressed as p/s/cm2/sr.

Previously, Natarajan and colleagues have demonstrated the feasibility of small interfering RNA therapy for attenuating myocardial ischemia reperfusion injury. However, subsequent analysis showed that the actual knockdown target was to murine procollagen prolyl 4-hydroxylase-2 rather than HIF prolyl 4-hydroxylase-2.[14] Here we confirmed our selection target with the GenBank database. Instead of using small interfering RNA fragments, which are only stable in vivo for 72 hours, we selected shRNA plasmid. However, at present, the duration of shRNA-mediated expression is unknown. Thus, we incorporated the 5xHRE-SV40-driving Fluc gene to track the shRNA expression activity. To evaluate the pharmacokinetics of shRNA in vivo, we injected the 2 shRNA plasmids into mice with myocardial infarction and followed their gene expression by Fluc bioluminescence imaging (FIG. 4A). As expected, mice injected with shPHD2 plasmid (bottom row) had significantly higher Fluc activity compared with mice injected with shScramble plasmid (top row). This can be attributed to the efficient knockdown of PHD2, resulting in more HIF-1α protein binding to the 5XHRE-Sv40 promoter site. For control animals injected with shScramble, endogenous activation of HIF-1α after myocardial infarction led to visible but lower Fluc signals. Quantitative analyses of the Fluc activities for both groups are shown in FIG. 4B. Overall, infracted animals had significantly higher activation of Fluc compared with noninfarcted animals during the first 2- to 4-week period.

Figure 8:
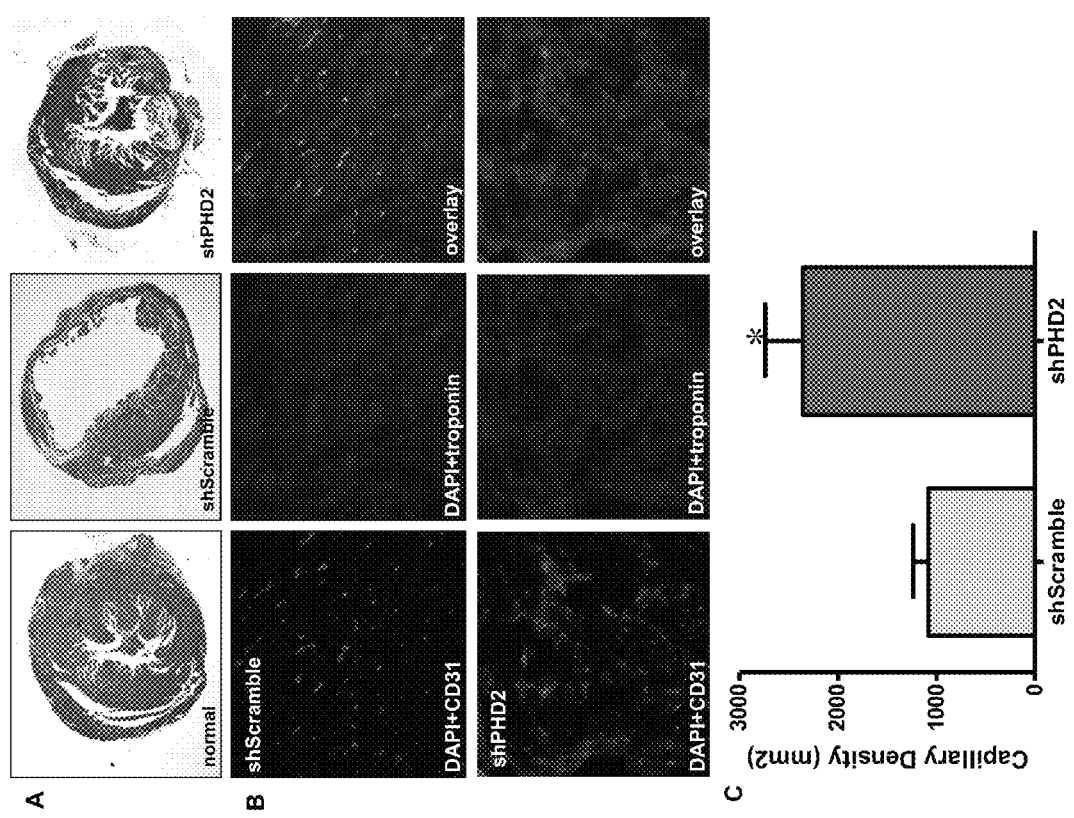
FIG. 8. A, Representative histology of infarcted heart injected with shScramble, infarcted heart injected with shPHD2, and control non-infarcted heart injected with PBS at week 4. Trichrome stains of the peri-infarct area indicate the infarction size based on collagen staining. B, Immunofluorescence staining of CD31 endothelial marker (green) indicate small vessels in the myocardium. Cardiomyocyte staining is identified by troponin (red; 400× magnification). Nuclear staining is identified by DAPI (blue; 400× magnification). C, Quantitative analysis of capillary density was significantly higher in the shPHD2 group compared with the control shScramble group at week 4 (P<0.01) (20× magnification).
Figure 10A:
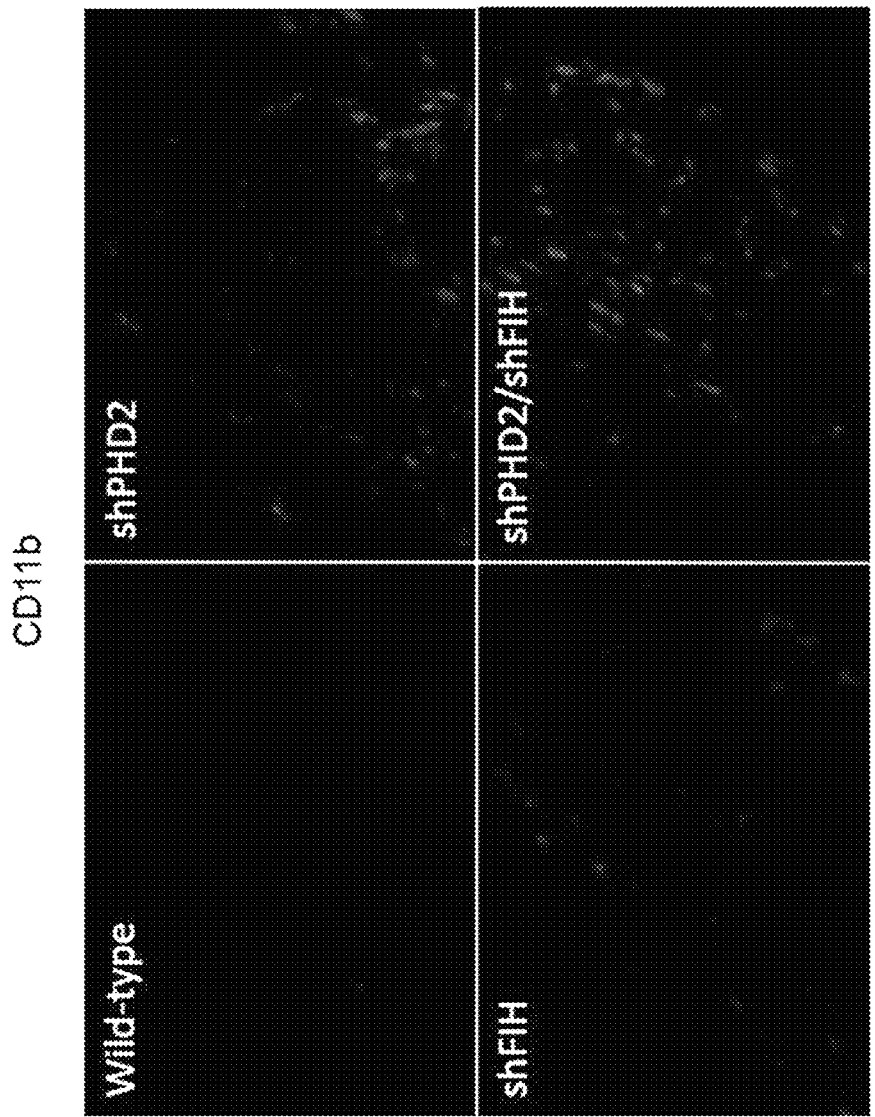
FIGS. 10A and 10B. Bone marrow-derived cells are recruited when PHD2 is silenced in a HIF-1α-independent manner to contribute to the vasculature. Wild-type HCT116 cells (human colon carcinoma cell line), HCT1116 cells expressing a shRNA to PHD2, HIF-1α, or expressing a combination of shRNAs to PHD2 and HIF-1α were implanted into the flank of CB17/scid mice and allowed to grow. Tumors were excised, sectioned and stained for CD11b (red) (10A) and CD45 (green) (10B), both markers of bone marrow-derived cells. Sections were counterstained with DAPI (blue). Scale bars represent 100 microns.
Figure 10B:
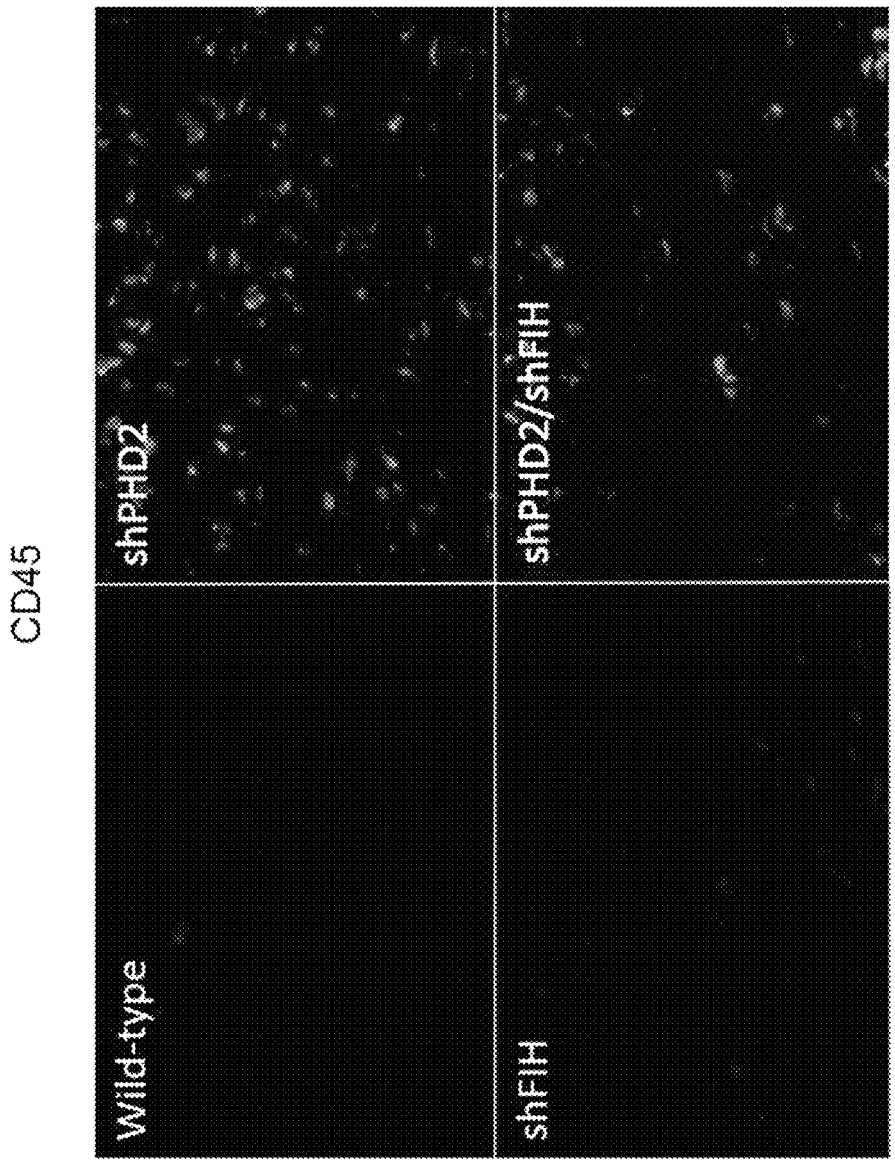
Figure 11:
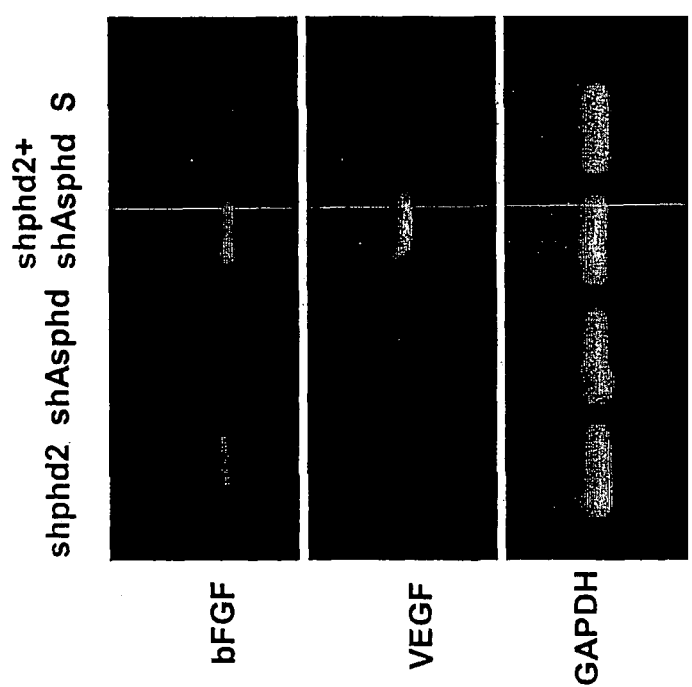
FIG. 11. RT-PCR showing knockdown with shPHD2 vs. shASPH vs. both in mouse C2C12 myoblasts. More robust activation of downstream pathway (bFGF and VEGF) is seen with double knockdown.

Injection of Short Hairpin Prolyl Hydroxylase-2 Plasmid Improved Left Ventricular Ejection Function To examined whether shPHD2 therapy can also improve cardiac function after myocardial infarction, echocardiography was performed before (Day −7) and after (Week 2, Week 4, Week 8) the left anterior descending artery ligation. At day −7, there was comparable LVFS between the shPHD2 group and shScramble control group. After left anterior descending artery ligation, the shPHD2 group had significantly higher LVFS(P=0.03) compared with the shScramble control group at Week 2 and Week 4 (FIG. 7). However, this beneficial effect was no longer maintained by week 8 (shPHD2: 38.3±3.8% versus shScramble: 36.8±2.1%; P=0.23). This is likely due to the limited short-term expression of plasmid-mediated shRNA expression within the first 4 weeks only, as shown by our imaging results (FIG. 7). To confirm the functional imaging data, trichrome staining showed less infarction size for the shPHD2 group compared with the shScramble group at Week 4. Immunohistochemistry of the pen-infarct region by CD31 staining also showed more neovascularization for the shPHD2 group compared with the shScramble group (FIG. 8).

Short Hairpin Prolyl Hydroxylase-2 Knockdown Mediates Hypoxia Inducible Factor-1 Alpha Upregulation in Myocardial Tissues.

Figure 5:
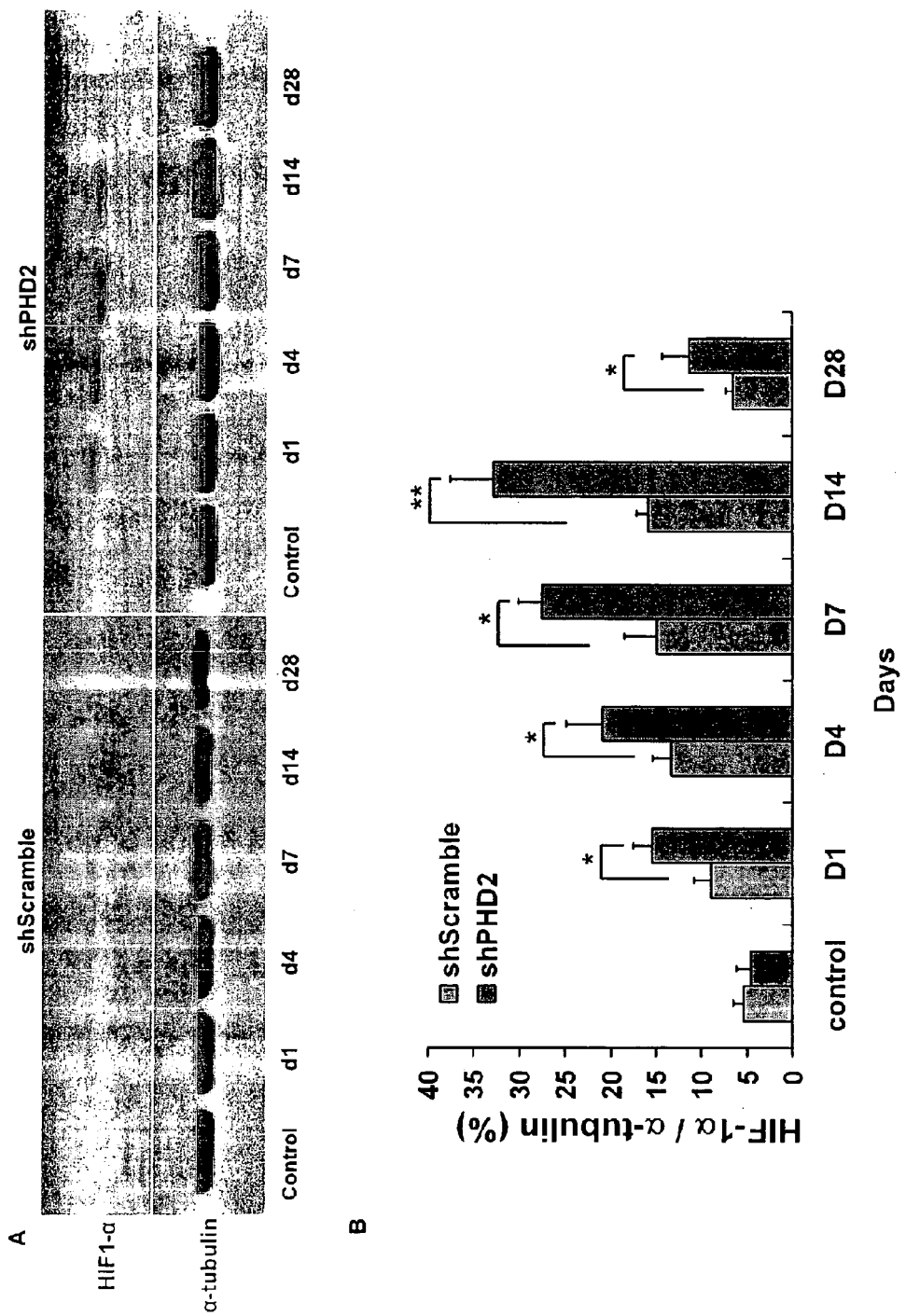
FIG. 5. Confirmation of HIF-1α activation in postmortem explanted hearts. A, Western blots for Day 1, Day 4, Day 7, Day 14, and Day 28 heart samples injected with shScramble (left) versus shPHD2 (right). Significant upregulation of HIF-1α can be seen in the shPHD2 therapy group within the first 2 weeks, coinciding with more robust Fluc bioluminescence imaging signal during the same time period. B, Quantitative densitometric analysis of HIF-1α protein levels after shScramble and shPHD2 injections show a similar trend compared to the in vivo imaging results from FIG. 4.

To further confirm the in vivo imaging data, we assayed for HIF-1α protein expression of explanted hearts at Day 1, Day 4, Day 7, Day 14, and Day 28 after shPHD2 plasmid therapy (FIG. 5A). Quantitative analysis of the Western blot indicates that HIF-1α proteins were significantly higher in the shPHD2-treated hearts compared with shScramble-treated hearts starting at Day 1. Protein levels peaked at Day 14 and returned back to baseline levels by Week 4 (FIG. 5B).

4. Discussion

Described herein is a novel shRNA therapy method, which can also be tracked by noninvasive molecular imaging in a murine model of myocardial infarction. The major findings can be concluded as follows: (1) shRNA can be expressed consistently with 2 H1 promoters driving sense and antisense fragments, respectively. The sense and antisense fragments anneal automatically in cytoplasm to exert their knocking down effects; (2) downregulation of the mouse PHD2 gene by plasmid-mediated shRNA interference (shPHD2) leads to activation of downstream angiogenic genes and proteins involved in the hypoxia response pathway as assessed by both in vitro and in vivo assays; (3) direct injection of shRNA targeting PHD2 can improve ventricular function and enhance neo-angiogenesis in a mouse model of myocardial infarction during 4-week follow-up; (4) importantly, the pharmacokinetics of shRNA plasmid delivery can be monitored noninvasively in living subjects by a novel 5XHRE-SV40 binding site driving Fluc reporter gene; (5) intramyocardial delivery of plasmid can lead to extracardiac leakage and expression of Fluc transgene in other organs such as the liver and lung; and (6) finally, a time-dependent decrease of Fluc signal activity was observed within a 4-week period due to plasmid degradation, which likely explains the loss of cardiac functional recovery at 8-week follow-up.

RNA interference is an innate biological phenomenon that has evolved during mammalian evolution.[15] Biologically, RNA interference has an important role for the transient and long-term blocking of protein expression. It is achieved by loading the RNA interference silencing complex with a short single-stranded antisense RNA that is complementary to a target mRNA.[16,17] In this study, we selected PHD2 as the knockdown target. PHD2 is an upstream negative regulatory gene in HIF-1 pathway. During hypoxia, when HIF-1α is stabilized, HIF-1 mediates transcriptional responses by binding to HREs present on a series of target genes involved in metabolic adaptation, hematopoiesis, angiogenesis, and apoptosis.[8,18] Under normal oxygenated conditions, HIF-1α is hydroxylated on 2 conserved proline residues, proline 402 or proline 564, by a family of prolyl-4-hydroxylases.[19-21] Several studies have demonstrated that prolyl-4-hydroxylase inhibition recapitulates various cellular and physiology responses to hypoxia or preconditioning stimuli. These include HIF-1α stabilization, the induction of hypoxia inducible genes (e.g., HO-1 and GLUT-1), stimulation of angiogenesis, and protection against metabolic stress.[22] Importantly, recent evidence suggests that the expression of a single angiogenic factor such as vascular endothelial growth factor alone may not be sufficient for the functional revascularization of ischemic tissues.[7] Thus, newer approaches based on upregulation of the upstream transcriptional factor HIF-1 may be a more natural choice. HIF-1 is known to control the expression of over 60 genes that affect cell survival and metabolism in adverse conditions.[3] Based on those previous studies, HIF-1 plays a critical role in a variety of physiological processes, and upregulation of HIF-1α through PHD2 knockdown represents a potentially new target in the field of cardiovascular gene therapy.

In this study, we were able to track the HIF-1α upregulation through a novel noninvasive molecular imaging approach, avoiding the sampling biases and errors that may occur when different groups of animals are euthanized at different time points. Five XHRE-SV40 promoter was inserted in front of the Fluc reporter gene. This hypoxia sensing construct can reflect the effects of shRNA plasmid expression through HIF-1α binding to the HRE element. For in vivo imaging signals, the plasmid expression reached peak activities between Week 1 and Week 2 (FIG. 4A). These results concur with the Western blot data of explanted hearts shown in FIG. 5A, which indicate that the HIF-1α activity (upregulated by shPHD2 knockdown) also increased during Week 1 to Week 2 and became degraded by Week 4. Furthermore, the echocardiographic data showed improvement of heart function within the first month, confirming the Western blot and molecular imaging results. However, we also observed a time-dependent decrease of bioluminescence signal activity within this time period, indicating a loss of the shRNA plasmid. Thus, adoption of newer vectors that are less immunogenic such as minicircles[23,24] or adenoassociated virus[25] may prolong gene expression and provide a more persistent functional recovery.

In summary, nonviral gene therapy through shRNA is a rapidly evolving area of investigation. With further validation, knocking down one or more regulatory factors involved in angiogenesis pathways as described here could provide a new avenue for treating myocardial ischemia. Furthermore, molecular imaging can be a valuable tool in monitoring the localization and activity of the shRNA vectors used for cardiovascular therapy. The in vivo information gathered is already generating useful insights and will enable better understanding of shRNA activity and mechanism in living subjects.

REFERENCES

1. Rosamond W, et al. Heart disease and stroke statistics—2007 update: a report from the American Heart Association Statistics Committee and Stroke Statistics Subcommittee. *Circulation.* 2007; 115:e69-171.
2. Kim M C, et al. Refractory angina pectoris: mechanism and therapeutic options. *J Am Coll Cardiol.* 2002; 39:923-934.
3. Yla-Herttuala S, et al. Gene transfer as a tool to induce therapeutic vascular growth. *Nat. Med.* 2003; 9:694-701.
4. Grines C L, et al. Angiogenic Gene Therapy (AGENT) Trial in patients with stable angina pectoris. *Circulation.* 2002; 105:1291-1297.
5. Hedman A, et al. Safety and feasibility of catheter-based local intracoronary vascular endothelial growth factor gene transfer in the prevention of postangioplasty and in-stent restenosis and in the treatment of chronic myocardial ischemia: phase II results of the Kuopio Angiogenesis Trial (KAT). *Circulation.* 2003; 107:2677-2683.
6. Henry T D, et al. The VIVA trial: Vascular endothelial growth factor in Ischemia for Vascular Angiogenesis. *Circulation.* 2003; 107:1359-1365.
7. Pislaru S, et al. Defining gene transfer before expecting gene therapy: putting the horse before the cart. *Circulation.* 2002; 106:631-636.
8. Lee J W, et al. Hypoxia-inducible factor (HIF-1) alpha: its protein stability and biological functions. *Exp Mol Med.* 2004; 36:1-12.
9. Miyagishi M, et al. U6 promoter-driven siRNAs with four uridine 3' overhangs efficiently suppress targeted gene expression in mammalian cells. *Nat Biotechnol.* 2002; 20:497-500.
10. Cao F, et al. In vivo visualization of embryonic stem cell survival, proliferation, and migration after cardiac delivery. *Circulation.* 2006; 113:1005-1014.
11. Wu J C, et al., Noninvasive optical imaging of firefly luciferase reporter gene expression in skeletal muscles of living mice. *Mol Ther.* 2001; 4:297-306.
12. Ruan H, et al. A hypoxiaregulated adeno-associated virus vector for cancer-specific gene therapy. *Neoplasia.* 2001; 3:255-263.
13. Brahimi-Horn et al. J. Hypoxia: the tumor's gateway to progression along the angiogenic pathway. *Trends Cell Biol.* 2001; 11: S32-S36.
14. Natarajan R et al., Hypoxia Inducible Factor-1 Activation by Prolyl 4-Hydroxylase-2 Gene Silencing Attenuates Myocardial Ischemia Reperfusion Injury. Cir. Res. 2006; 98: 133-140.
15. Grimm D, et al. Fatality in mice due to oversaturation of cellular microRNA/short hairpin RNA pathways. *Nature.* 2006; 441: 537-541.
16. Gou D, et al. Gene silencing in alveolar type II cells using cell-specific promoter in vitro and in vivo. *Nucleic Acids Res.* 2004; 32:e134.
17. Hannon G J. RNA interference. *Nature.* 2002; 418:244-251.
18. Indovina P, et al. Three-dimensional cell organization leads to almost immediate HRE activity as demonstrated by molecular imaging of MG-63 spheroids using two-photon excitation microscopy. *FEBS Lett.* 2007; 581:719-726.
19. Chan D A, et al. Hypoxia, gene expression, and metastasis. *Cancer Metastasis Rev.* 2007; 26:333-339.
20. Chan D A, et al. Role of prolyl hydroxylation in oncogenically stabilized hypoxia-inducible factor-1alpha. *J Biol. Chem.* 2002; 277:40112-40117
21. Chan D A, et al. Coordinate regulation of the oxygen-dependent degradation domains of hypoxia-inducible factor 1 alpha. *Mol Cell Biol.* 2005; 25:6415-6426.

22. Hirota K, et al. Regulation of hypoxia-inducible factor 1 by prolyl and asparaginyl hydroxylases. *Biochem Biophys Res Commun.* 2005; 338:610-616.
23. Chen Z-Y, et al. Improved production and purification of minicircle DNA vector free of plasmid bacterial sequences and capable of persistent transgene expression in vivo. *Hum Gene Ther.* 2005; 16: 126-131.
24. Chen Z-Y, et al. Minicircle DNA vectors devoid of bacterial DNA result in persistent and high-level transgene expression in vivo. *Mol Ther.* 2003; 8:495-500.
25. Su H, et al. AAV serotype-1 mediates early onset of gene expression in mouse hearts and results in better therapeutic effect. Gene Ther. 2006; 13:1495-1502.
26. Huang, M, et al. Short Hairpin RNA Interference Therapy for Ischemic Heart Disease. *Circulation.* 2008; 118: to be determined.
27. Pekkala et al., The Peptide-substrate-binding Domain of Collagen Prolyl 4-Hydroxylases is a Tetratricopeptide Repeat Domain with Functional Aromatic Residues. J B C 2004; 279(50): 52255-52261.
28. See, www.nlm.nih.gov/medlineplus.com
29. See, www.emedicinehealth.com
30. Dinchuk J E, et al. Aspartyl beta-hydroxylase (Asph) and an evolutionarily conserved isoform of Asph missing the catalytic domain share exons with junction. *J Biol. Chem.* 2000 Dec. 15; 975(50):19543-54.
31. Song et al., RNA interference targeting Fas protects mice from fulminant hepatitis. *Nature Medicine,* 9:347-351 (2003).

All references, including publications, patent applications, and patents, cited herein are hereby incorporated by reference in their entirety to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating ischemic heart disease in a mammal, and monitoring progress thereof by imaging, which method comprises the steps of:
   a) administering to heart tissue of the mammal in need of said treatment an effective amount of a vector in a pharmaceutically-acceptable carrier, the vector comprising, in operable linkage:
      i) a promoter; and
      ii) at least one polynucleotide encoding at least two small hairpin RNAs (shRNAs), which are shPHD2 and shASPHD;
   wherein upon expression of the vector, neo-angiogenesis is induced in the heart tissue, thereby treating the mammal's ischemic heart disease; and
   b) monitoring progress of the treatment in step a) by imaging.

2. The method of claim 1, wherein the nucleotide sequence encoding shPHD2 is 5'-GTACAGCCACGATACGCCA-3' (SEQ ID NO: 9).

3. The method of claim 1, wherein the nucleotide sequence encoding shPHD2 is 5'-AGACTGGGACGCCAAGGTA-3' (SEQ ID NO: 10).

4. The method of claim 1, wherein the vector further comprises, in operable linkage, in addition to the promoter, an HIF-1α responsive element and a reporter gene.

5. The method of claim 4, wherein the HIF-1α responsive element is one or more copies of a hypoxia response element (HRE).

6. The method of claim 5, wherein the HIF-1α responsive element comprises five copies of the HRE element.

7. The method of claim 4, wherein the reporter gene is a firefly luciferase (Fluc) gene.

8. The method of claim 4, wherein the imaging comprises monitoring the mammal for level of at least PHD2 by detecting a presence or absence of a detectable signal from the reporter gene.

9. The method of claim 1, which further comprises a second administration of the vector.

10. The method of claim 1, wherein the mammal is a human.

11. The method of claim 1, wherein the vector comprises more than one polynucleotide encoding the at least two shRNAs.

12. A method of treating a disease or disorder in a mammal by double knockdown, and monitoring progress of the treatment by imaging; which comprises the steps of:
   a) administering to the mammal in need of the treatment an effective amount of a vector in a pharmaceutically-acceptable carrier, the vector comprising, in operable linkage:
      i) a promoter, an HIF-1α responsive element, and a reporter gene; and
      ii) at least one polynucleotide encoding at least two small hairpin RNA (shRNA), which are shPHD2 and shASPHD;
   wherein upon expression of the vector, expression of PHD2 and ASPHD are both knocked down, thereby treating the disease or disorder of the mammal; and
   b) monitoring progress of the treatment by imaging.

13. The method of claim 12, wherein the disease or disorder is selected from the group consisting of ischemic heart disease, peripheral vascular disease and decubitis ulcer.

14. The method of claim 12, wherein the nucleotide sequence encoding shPHD2 is 5'-GTACAGCCAGCATACGCA-3' (SEQ ID NO: 9).

15. The method of claim 12, wherein the nucleotide sequence encoding shPHD2 is 5'-AGACTGGGACGCCAAGGTA-3' (SEQ ID NO: 10).

16. The method of claim 12, wherein the HIF-1α responsive element is one or more copies of a hypoxia response element (HRE).

17. The method of claim 16, wherein the HIF-1α responsive element comprises five copies of the HRE element.

18. The method of claim 12, wherein the reporter gene is a firefly luciferase (Fluc) gene.

19. The method of claim 12, wherein the monitoring comprises detecting accumulation at least PHD2 by a presence or absence of a detectable signal from the reporter gene.

20. The method of claim 12, wherein the mammal is a human.

21. The method of claim 12, which further comprises administering said vector an additional time.

22. The method of claim 1, wherein the nucleotide encoding shASPHD has the sequence for shASPHD-3: 5'-TGGGAGAAGAGGAGGCATT-3' (SEQ ID NO: 14).

23. The method of claim 1, wherein the nucleotide encoding shASPHD has the sequence For shASPHD-4: 5'-GAGGAGGGATTTCAGGAGG-3' (SEQ ID NO: 15).

24. The method of claim 1, wherein the at least one polynucleotide comprises a sense strand corresponding to a portion of the mRNA transcript of PHD2 selected from the group consisting of SEQ ID NO: 2, SEQ ID NO: 4 and SEQ IQ NO: 6, which are human transcript variants.

* * * * *